(12) United States Patent
Luan et al.

(10) Patent No.: US 12,194,190 B2
(45) Date of Patent: Jan. 14, 2025

(54) MEDICAL ADHESIVE AND PREPARATION METHOD THEREOF

(71) Applicant: CHANGCHUN INSTITUTE OF APPLIED CHEMISTRY, CHINESE ACADEMY OF SCIENCE, Jilin (CN)

(72) Inventors: Shifang Luan, Jilin (CN); Ran Yang, Jilin (CN); Xu Zhang, Jilin (CN); Binggang Chen, Jilin (CN); Qiuyan Yan, Jilin (CN)

(73) Assignee: CHANGCHUN INSTITUTE OF APPLIED CHEMISTRY, CHINESE ACADEMY OF SCIENCE, Jilin (CN)

( * ) Notice: Subject to any disclaimer, the term of this patent is extended or adjusted under 35 U.S.C. 154(b) by 124 days.

(21) Appl. No.: 17/984,291

(22) Filed: Nov. 10, 2022

(65) Prior Publication Data
US 2023/0211043 A1    Jul. 6, 2023

(30) Foreign Application Priority Data

Dec. 31, 2021  (CN) .......................... 202111677247.3
Dec. 31, 2021  (CN) .......................... 202111677252.4
Dec. 31, 2021  (CN) .......................... 202111677281.0
Dec. 31, 2021  (CN) .......................... 202111677282.5

(51) Int. Cl.
A61L 24/06       (2006.01)
A61L 24/00       (2006.01)

(52) U.S. Cl.
CPC ........... *A61L 24/06* (2013.01); *A61L 24/0015* (2013.01); *A61L 24/0042* (2013.01); *A61L 2300/102* (2013.01); *A61L 2300/104* (2013.01); *A61L 2300/112* (2013.01); *A61L 2300/204* (2013.01); *A61L 2300/208* (2013.01); *A61L 2300/216* (2013.01); *A61L 2300/254* (2013.01); *A61L 2300/404* (2013.01); *A61L 2300/412* (2013.01); *A61L 2400/04* (2013.01); *A61L 2430/02* (2013.01)

(58) Field of Classification Search
None
See application file for complete search history.

(56) References Cited

U.S. PATENT DOCUMENTS

| 5,541,275 A | 7/1996 | Fleischmann et al. | |
| 2005/0080195 A1 * | 4/2005 | Iwama | C08L 33/00 |
| | | | 525/228 |

FOREIGN PATENT DOCUMENTS

| CN | 100998889 A | 7/2007 |
| CN | 103467728 A | 12/2013 |
| CN | 103585671 A | 2/2014 |
| CN | 104958781 A | 10/2015 |
| CN | 107343965 A | 11/2017 |
| CN | 107602762 A | 1/2018 |
| CN | 109675093 A | 4/2019 |
| CN | 110124111 A | 8/2019 |
| CN | 110548171 A | 12/2019 |
| CN | 111840631 A | 10/2020 |
| CN | 112023109 A | 12/2020 |
| EP | 4001345 A1 | 5/2022 |
| JP | 2006232890 A | 9/2006 |
| WO | 2021008602 A1 | 1/2021 |

OTHER PUBLICATIONS

Polymer Chemistry, Xiao Chaobo et al., Wuhan University Press, Dec. 31, 1998, pp. 135-139.
The 1st Office Action dated Oct. 22, 2024 for the Chinese Patent Application No. CN202111677281.0. English Translation of the 1st Office Action Provided by http://globaldossier.uspto.gov.
Redox Initiators, Chaobo XIAO et al., Polymer Chemistry, Published by Wuhan University Press, Dec. 31, 1998, pp. 135-139.
The 1st Office Action dated Oct. 28, 2024 for the Chinese Patent Application No. CN202111677247.3. English Translation of the 1st Office Action Provided by http://globaldossier.uspto.gov.
The 1st Office Action dated Oct. 28, 2024 for the Chinese Patent Application No. CN202111677252.4. English Translation of the 1st Office Action Provided by http://globaldossier.uspto.gov.
The 1st Office Action dated Oct. 28, 2024 for the Chinese Patent Application No. CN202111677282.5. English Translation of the 1st Office Action Provided by http://globaldossier.uspto.gov.

* cited by examiner

*Primary Examiner* — David J Blanchard
*Assistant Examiner* — Daniel F Coughlin
(74) *Attorney, Agent, or Firm* — Yue (Robert) Xu; Apex Attorneys at Law, LLP

(57) ABSTRACT

The present disclosure provides a medical adhesive and a preparation method thereof, comprising a component A and a component B: the component A comprises a cycloketene acetal compound and an oxidizing agent; the component B comprises a vinyl monomer, a cross-linking agent and a reducing agent, wherein the cycloketene acetal compound is selected from one or more of 2-methylene-1,3-dioxepane, 2-methylene-4-phenyl-1,3-dioxolane, 5,6-benzo-2-methylene-1,3-dioxepane and 4,7-dimethyl-2-methylene-1,3-dioxepane. The medical adhesive overcomes the disadvantages of conventional medical adhesives.

17 Claims, 6 Drawing Sheets

MEDICAL ADHESIVE AND PREPARATION METHOD THEREOF

FIELD

The present disclosure relates to the field of medical adhesive.

BACKGROUND

Medical adhesives are new medical materials used for adhesion of parts of organisms during surgical operations. Medical adhesives can be used for surgical fixation of fractures, and can also be used for the adhesion of skin, organs, nerves, blood vessels, mucous membranes and other parts. Traditional medical adhesives include cyanoacrylate, polymethacrylate, etc., but they have the problems of high hardness, poor toughness, and repeated wear and tear causing tissue damage. In addition, traditional medical adhesives also have toxic side effects on organism tissues and poor degradability, which also easily lead to infection of tissue sites.

An ideal medical adhesive should have one or more of the following properties: (1) it is safe and non-toxic; (2) it has good biocompatibility; (3) it is sterile and can be kept sterile for a certain period of time; (4) it can achieve fast adhesion under normal temperature and normal pressure; (5) it has good adhesion strength and durability, and the adhesion part has certain elasticity and toughness; (6) it is non-irritating to human tissues during its use; (7) after reaching the effect, it can be gradually degraded, absorbed and metabolized.

At present, traditional medical adhesives all have some shortcomings and cannot meet the above requirements. Therefore, it is urgent to develop a medical adhesive that meets the corresponding application requirements.

SUMMARY

One of the objectives of the present disclosure is to provide a fast-curing and degradable strong bone adhesive and a preparation method thereof. The bone adhesive has osteogenic activity, and has features of fast curing, high adhesion strength and biodegradability.

The traditional cyanoacrylate medical adhesive has the advantages of fast curing and good instant adhesion strength, especially suitable for the adhesion of comminuted fractures. However, its polymer product is hard and brittle, which is easy to fall off when used in a wet environment in vivo for a long time, eventually leading to failure; moreover, it will release toxic substances such as formaldehyde and the like during its use, which has toxic side effects on organism tissues. The polymer product is difficult to be degraded, which greatly hinders the healing of bone tissue and is not conducive to bone tissue regeneration.

In order to solve the above problems, Chinese invention patent CN201310548359.8 discloses a preparation method of adding a formaldehyde inhibitor to a cyanoacrylate medical adhesive, which effectively reduces the concentration of formaldehyde during its use and improves the toughness of the adhesive film. Although it has reached the clinical use standard of medical tissue adhesives, its problem of refractory degradation still exists, which will hinder bone healing and limit its application in bone adhesion. Chinese invention patents CN201610298783.5 and CN201710972350.8 respectively disclose a porous bone adhesive and a preparation method thereof. By introducing bioactive particles/polymer pore-forming agent composite particles into traditional cyanoacrylate, using the gradual dissolution and degradation of pore-forming agent component after implanted in the body, a porous structure is formed in situ, which relieves the obstruction of cyanoacrylate adhesive to the healing of bone tissue. However, the problems of the adhesion stability of the material and the refractory degradation of the main material still exist. In order to solve the problem of degradability of bone adhesive, many works have introduced natural polymer to improve the degradability of the adhesive. For example, Chinese invention patent 201910555536.2 discloses a bone adhesive of a gelatin-based hydrogel form. Although the material is biodegradable, the pretreatment of the material is cumbersome and complex, and the adhesion and mechanical strength thereof are far less than that of the synthetic adhesives.

The fast-curing and degradable strong bone adhesive of the present disclosure solves the above problems, which has osteogenic activity, and has the characteristics of fast curing, high adhesion strength and biodegradability.

In one embodiment, the present disclosure provides a fast-curing and degradable strong bone adhesive comprising a component A and a component B:

The component A comprises a cycloketene acetal compound and an oxidizing agent;

The component B comprises a vinyl monomer, a cross-linking agent and a reducing agent.

The strong bone adhesive provided by the present disclosure comprises a component A, wherein the component A comprises a cycloketene acetal compound and an oxidizing agent; the cycloketene acetal compound is selected from one or more of 2-methylene-1,3-dioxepane (MDO), 2-methylene-4-phenyl-1,3-dioxolane (MPDL), 5,6-benzo-2-methylene-1,3-dioxepane (BMDO) and 4,7-dimethyl-2-methylene-1,3-dioxepane (DMMDO).

The 2-methylene-1,3-dioxepane (MDO) has the structure of formula 101:

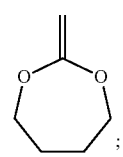

formula 101

The 2-methylene-4-phenyl-1,3-dioxolane (MPDL) has the structure of formula 102:

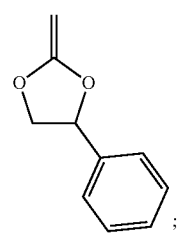

formula 102

The 5,6-benzo-2-methylene-1,3-dioxepane (BMDO) has the structure of formula 103:

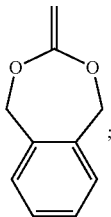

formula 103

The 4,7-dimethyl-2-methylene-1,3-dioxepane (DMMDO) has the structure of formula 104:

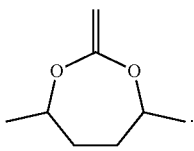

formula 104

FIG. 1 is the schematic diagram of the structural formula of cycloketene acetal compounds.

The oxidizing agent is selected from one or more of benzoyl peroxide, tert-butyl hydroperoxide, ammonium persulfate and hydrogen peroxide.

The preparation raw material provided by the present disclosure comprises a component B, wherein the component B comprises a vinyl monomer, a cross-linking agent and a reducing agent; the vinyl monomer is selected from one or more of (meth)acrylic acid, (meth)acrylate, vinyl acetate, maleimide polyethylene glycol carboxylic acid, biotin-PEG-6-maleimide, m-maleimidobenzoyl-N-hydroxysulfosuccinimide ester, 6-maleimidohexanoic acid, ethylene glycol vinyl ether, tetramethylene glycol monovinyl ether, vinyl (2-chloroethyl) ether, (meth)acryloyloxyphosphorylcholine, 10-(phosphonooxy)decyl methacrylate, sulfobetaine methacrylate, 4-methacryloyloxyethyl trimellitic anhydride, dopamine methacrylamide, N-acryloyl(trimethylol)amino methane, poly(ethylene glycol) methacrylate, 2-(N,N-dimethylamino)ethyl methacrylate, (meth)allylamine and O-allylhydroxylamine.

The cross-linking agent is selected from one or more of ethylene glycol dimethacrylate, methacrylic anhydride, diallyl maleate, bis(2-methacryloxyethyl)phosphate, tri(ethylene glycol)divinyl ether, diallylamine, triallylamine, N-methyldiallylamine, 1,5-hexadiene, diallyl disulfide and diallyldimethylsilane.

In the present disclosure, the reducing agent is selected from one or more of N,N-dimethyl-p-toluidine, N,N-dimethylaniline, sodium metabisulfite, sodium bisulfite and ferrous sulfate.

In the present disclosure, the molar ratio of the cycloketene acetal compound to the vinyl monomer is 100:1 to 1:100; preferably 10:1 to 1:10, more preferably 1:1 to 1:2.

The mass of the cross-linking agent accounts for 0.2 wt % to 60 wt % of the total mass of the cycloketene acetal compound and the vinyl monomer, preferably 0.5 wt % to 10 wt %, more preferably 1 wt % to 5 wt %.

In the present disclosure, the component B in the strong bone adhesive preferably further comprises an osteogenic active ingredient;

The osteogenic active ingredient is selected from one or more of hydroxyapatite, calcium triphosphate, bioactive glass, mesoporous silica, BMP-2, BMP-7, strontium ion, zinc ion, magnesium ion, bisphosphonate, dexamethasone, tacrolimus, and simvastatin;

The osteogenic active ingredient accounts for 0.01 wt % to 100 wt % of the cycloketene acetal compound, preferably 5 wt % to 50 wt %, and more preferably 10 wt % to 30 wt %.

In the present disclosure, the mole number of the oxidizing agent accounts for 0.01% to 10% of the total mole number of the cycloketene acetal compound and the vinyl monomer, preferably 0.1% to 5%, more preferably 0.2% to 2%.

In the present disclosure, the mole number of the reducing agent accounts for 0.01% to 10% of the total mole number of the cycloketene acetal compound and vinyl monomer, preferably 0.1% to 5%, more preferably 0.2% to 2%.

In the present disclosure, after free-radical polymerization of the components, the main chain contains a structure of ester bond.

The present disclosure also provides a preparation method of the strong bone adhesive according to the above technical solution, comprising the following steps:

Dissolving an oxidizing agent in a cycloketene acetal compound to obtain a mixed solution A;

Then uniformly mixing a vinyl monomer, a cross-linking agent and a reducing agent to obtain a mixed solution B; and Uniformly mixing the above mixed solution A and mixed solution B, and in-situ curing the mixture to obtain a strong bone adhesive.

The duration of the mixing of the mixed solution A and the mixed solution B of the present disclosure is 1-600 s, preferably 1-300 s, and more preferably 1-30 s. After the mixed solution A and the mixed solution B are mixed, a polymerization reaction occurs, during which the temperature of the polymerization reaction is not higher than 50° C., preferably not higher than 40° C., more preferably not higher than 37° C. The polymerization reaction is a ring-opening polymerization reaction based on free radicals as the active center.

If the osteogenic active ingredient needs to be added, in the present disclosure, preferably the vinyl monomer, the cross-linking agent, the osteogenic active ingredient and the reducing agent are mixed uniformly.

In the present disclosure, the strong bone adhesive is coated on the fracture surface of the bone tissue; the duration of the coating is 1-600 s, preferably 1-60 s, more preferably 1-30 s. The fracture surface of the bone tissue may be a flat surface or any irregular sectional surface.

In the present disclosure, after coating the strong bone adhesive on the fracture surface of the bone tissue, the duration of fixing the bone is more than 30 s, preferably more than 180 s, more preferably more than 600 s.

Compared with the prior art, the beneficial effects of the technical solutions provided by the present disclosure are as follows: (1) In the present disclosure, the strong bone adhesive is formed by in-situ curing of free radical ring-opening polymerization under the initiation of a highly active redox system, the whole process of which can be carried out in a mild environment (≤37° C.), the reaction is rapid (cured within 1-3 min), and the reaction is slightly exothermic; (2) After ring-opening polymerization of cycloketene acetal compound, the main chain contains a structure of ester bond, which can be degraded in a physiological environment (8-week degradation rate>20%), and has good degradability; (3) The introduction of co-monomer and cross-linking agent makes the bone tissue adhesive constructed by the present disclosure have high mechanical strength and adhesion strength (adhesion strength within 10 min>1 MPa), which is not swollen in physiological environment, has good physiological stability, and can provide mechanical support for comminuted fractures. (4) The fast-curing degradable bone adhesive provided by the present disclosure has simple preparation method and is ready-to-use, which has a convenient use process, an appropriate implementation time window (1-5 min), and strong clinical maneuverability.

Another object of the present disclosure is to provide an absorbable rapid hemostatic adhesive and a preparation method thereof and application thereof, wherein the adhesive is formed by in-situ curing of free radical ring-opening polymerization under the initiation of a redox radical polymerization initiator, during which the adhesion closure is fast, and the reaction is slightly exothermic, which will not burn the human body.

In recent years, in response to the demand for rapid hemostasis, various hemostatic materials have appeared on the market, mainly including zeolite dressings, chitosan dressings, gelatin sponges, oxidized regenerated cellulose, etc. These materials have high water absorption rates and can quickly adhere to the wound to form a hemostatic microenvironment. The above-mentioned hemostatic materials have disadvantages such as low adhesion strength, slow speed, etc. α-cyanoacrylate adhesive has fast curing speed and high adhesion strength, which can solve the above problems. In the early 1960s, cyanoacrylate adhesives were all the rage, but when applied, the biological toxicity thereof limited their development. Studies have found that cyanoacrylate modified monomers such as isobutyl cyanoacrylate, n-butyl cyanoacrylate, and n-octyl cyanoacrylate and the like can be used to reduce the biological toxicity of the cyanoacrylate adhesives. This discovery has promoted the further development of medical soft tissue adhesives. However, at present, α-cyanoacrylate adhesives have a series of problems such as high hardness, poor toughness, repeated wear and tear causing tissue damage, premature detachment or rupture of adhesive films, and even reactive inflammatory reactions. Most seriously, its clinical application is limited due to its non-absorption. In addition, with the emergence of "super bacteria" caused by the abuse of antibiotics, purulent infection or specific bacterial infection of bleeding wound may lead to tetanus, sepsis, pyemia and toxemia, and even septic shock, all of which are causes of death that cannot be ignored. Therefore, the efficacy of new hemostatic materials should not only include strong coagulation ability, but also include antibacterial and anti-infection ability, so as to reduce the death of patients caused by postoperative infection, wound suppuration and other factors.

The absorbable rapid hemostatic adhesive of the present disclosure solves the above problems, and the absorbable rapid hemostatic adhesive has the following characteristics: fast closing speed of the bleeding wound, fast hemostatic speed, good biocompatibility, and absorbability by the human body.

In one embodiment, the present disclosure provides an absorbable rapid hemostatic adhesive comprising the following component A and component B:

The component A comprises a cycloketene acetal compound and an oxidizing agent;

The component B comprises a vinyl monomer, a cross-linking agent, a hemostatic agent and a reducing agent.

In the present disclosure, the cycloketene acetal compound is selected from one or more of 2-methylene-1,3-dioxepane (MIDO), 2-methylene-4-phenyl-1,3-dioxolane (MPDL), 5,6-benzo-2-methylene-1,3-dioxepane (BMDO) and 4,7-dimethyl-2-methylene-1,3-dioxepane (DMMDO).

The vinyl monomer is selected from one or more of (meth)acrylic acid, (meth)acrylate, vinyl acetate, maleimide polyethylene glycol carboxylic acid, biotin-PEG-6-maleimide, m-maleimidobenzoyl-N-hydroxysulfosuccinimide ester, 6-maleimidohexanoic acid, ethylene glycol vinyl ether, tetramethylene glycol monovinyl ether, vinyl(2-chloroethyl) ether, 2-methacryloyloxyethylphosphorylcholine, 10-(phosphonooxy)decyl methacrylate, sulfobetaine methacrylate, 4-methacryloyloxyethyl trimellitic anhydride, dopamine methacrylamide, N-acryloyl(trimethylol)aminomethane, poly(ethylene glycol) methacrylate, 2-(N,N-dimethylamino)ethyl methacrylate, (meth)allylamine and O-allylhydroxylamine. In specific embodiments, the vinyl monomer is selected from methacrylic acid (MA), poly(ethylene glycol) methacrylate (PEM), ethylene glycol vinyl ether or 2-methacryloyloxyethylphosphocholine.

In the present disclosure, the cross-linking agent is selected from monomers containing two vinyl units and/or monomers containing more than two vinyl units; the cross-linking agent is preferably selected from one or more of methacrylic anhydride, diallyl maleate, bis(2-methacryloxyethyl)phosphate, tri(ethylene glycol)divinyl ether, diallylamine, triallylamine, N-methyldiallylamine, 1,5-hexadiene, diallyl disulfide and diallyldimethylsilane. In a specific embodiment, the cross-linking agent is bis(2-methacryloxyethyl)phosphate.

In the present disclosure, the hemostatic agent is selected from one or more of vitamin k1, vitamin k4, haemocoagulase, sodium carboxysulfonate, aminocaproic acid, carbazochrome and halloysite.

In the present disclosure, the molar ratio of the vinyl monomer to the cycloketene acetal compound is 0.01 to 100:1; preferably 0.1 to 10:1;

The molar ratio of the cross-linking agent to the cycloketene acetal compound is 0.001 to 0.2:1; preferably 0.005 to 0.05:1

The molar ratio of the hemostatic agent to the cycloketene acetal compound is $1 \times 10^{-7}$ to $1 \times 10^{-4}:1$, preferably $1 \times 10^{-6}$ to $1 \times 10^{-5}:1$.

The component B of the absorbable rapid hemostatic adhesive provided by the present disclosure preferably further comprises an antibacterial agent; the antibacterial agent is selected from one or more of silver ions, zinc ions, antibacterial peptide, coumarin compound, polyguanidine polymers and benzalkonium chloride; the molar ratio of the antibacterial agent to the cycloketene acetal compound is $1 \times 10^{-7}$ to $1 \times 10^{-4}:1$, preferably $1 \times 10^{-5}$ to $1 \times 10^{-7}:1$.

In the present disclosure, the oxidizing agent is selected from one or more of benzoyl oxide, tert-butyl hydroperoxide, ammonium persulfate and hydrogen peroxide.

The reducing agent is selected from one or more of N,N-dimethyl-p-toluidine, sodium metabisulfite, sodium bisulfite and ferrous sulfate.

The molar ratio of the oxidizing agent to the cycloketene acetal compound is 0.001 to 0.2:1.

The molar ratio of the oxidizing agent to the reducing agent is 0.01 to 10:1.

The oxidizing agent is solid; the reducing agent is liquid.

The oxidizing agent in the component A and the reducing agent in the component B are used as redox radical polymerization initiators, and the in-situ curing is namely performing ring-opening polymerization reaction; the ring-opening polymerization reaction is carried out under the initiation of the redox radical polymerization initiator.

The present disclosure also provides a preparation method of the absorbable rapid hemostatic adhesive according to the above technical solution, comprising the following steps:
1) Mixing a cycloketene acetal compound and an oxidizing agent to obtain a component A;
Mixing a vinyl monomer, a cross-linking agent, a hemostatic agent and a reducing agent to obtain a component B;
2) Mixing the component A with the component B uniformly, and in-situ curing the mixture to obtain an absorbable rapid hemostatic adhesive.

In the present disclosure, the duration of the mixing of the component A with the component B is preferably 1-300 s, more preferably 5-20 s.

After the component A and the component B are mixed, the system undergoes an in-situ free radical ring-opening polymerization reaction, during which the temperature of the polymerization reaction is 30° C. to 50° C., preferably 35° C. to 38° C. The polymerization reaction is a ring-opening polymerization reaction based on free radicals as the active center. After the radical polymerization of the components, the main chain contains a structure of ester bond.

In order to improve the antibacterial effect, in the present disclosure, preferably an antibacterial agent is added to the component B.

The adhesive provided by the present disclosure comprises a component A and a component B. The component A and the component B are mixed, and then the mixture are quickly coated on a wound or a surgical incision of tissue, organ and skin, after which the in-situ free radical ring-opening polymerization reaction occurs quickly, so as to achieve the rapid adhesive closure of wounds or surgical incisions.

In the present disclosure, the duration of the coating is preferably 1-600 s, preferably 1-100 s, and more preferably 1-30 s.

The present disclosure provides an application of the absorbable rapid hemostatic adhesive according to the above technical solution or the absorbable rapid hemostatic adhesive prepared by the preparation method according to the above technical solution in the preparation of hemostatic products.

The present disclosure also provides a method for hemostasis, comprising applying the absorbable rapid hemostatic adhesive described in the above technical solution or the absorbable rapid hemostatic adhesive prepared by the preparation method described in the above technical solution to the site in need of hemostasis.

In the present disclosure, the site in need of hemostasis is skin, organs or blood vessels.

The present disclosure provides an absorbable rapid hemostatic adhesive, comprising a component A and a component B: the component A comprises a cycloketene acetal compound and an oxidizing agent; the component B comprises a vinyl monomer, a cross-linking agent, a hemostatic agent and a reducing agent. The adhesive provided by the present disclosure is formed by in-situ curing of free radical ring-opening polymerization under the initiation of a redox free radical polymerization initiator in the human body environment, during which the adhesion is fast, and the reaction is slightly exothermic, which will not burn the human body. After the free radical ring-opening polymerization of cycloketene acetal compound, the main chain contains a structure of ester bond, which can be degraded in a physiological environment with an 8-week degradation rate of more than 20%. The mild reaction conditions are conducive to the loading of the hemostatic agent and antibacterial agent. The gradual exposure and release of these substances further impart activated hemostatic efficacy to the adhesive and avoid bacterial infection. The adhesive is ready-to-use, and has a simple use process, an ideal implementation time window of 1-5 min, and strong clinical maneuverability.

In the present disclosure, the redox free radical polymerization initiator is added to the above substance mixture, and the obtained mixture are coated to the bleeding sites such as blood vessels, organs, skin, etc., then the rapid in-situ free radical ring-opening polymerization reaction occurs to realize the rapid closure and hemostasis. The hemostatic adhesive has a simple preparation method and is ready-to-use, which can achieve rapid adhesion closure of the bleeding wound, fast hemostasis by realizing hemostasis closure within 15 s, and has excellent biodegradability. The antibacterial agent is released along with the degradation of the adhesive, so as to avoid the occurring of bacterial infection.

Another object of the present disclosure is to provide an absorbable medical soft tissue adhesive, a preparation method thereof and application thereof, wherein the adhesive can be cured quickly, and have good degradability and high adhesion strength.

Soft tissue adhesives can be used for the adhesion of skin, organs, nerves, blood vessels, mucous membranes and other parts, most of which use medical α-cyanoacrylate adhesive, fibrin biological adhesive and hydrogel tissue adhesive. Since fibrin biological adhesive is produced in blood, during use there is a possibility of mutual infection of infectious diseases such as hepatitis, AIDS, etc. Although autologous blood can be used, it is not suitable for emergency treatment because its strength and speed are not ideal. Hydrogel tissue adhesives are formed by the process of the polymerization of polymers such as polyethylene glycol and the like, the degradation thereof will be accelerated under light conditions, seriously affecting their adhesive fastness. However, the α-cyanoacrylate adhesive avoids the shortcomings of fibrin biological adhesive and has a fast curing speed and good biocompatibility. Cyanoacrylate was first synthesized by Ardis in the 1940s, after a decade, an American company first discovered that cyanoacrylate had a good adhesive performance. Subsequently, Coover et al. found that such adhesive can be used in the adhesion of biological tissues, so it was used as a new type of medical soft tissue adhesive. In the early 1960s, cyanoacrylate adhesives were all the rage, but when applied, the biological toxicity thereof limited their development. After the 1970s, researchers found that cyanoacrylate modified monomers such as isobutyl cyanoacrylate, n-butyl cyanoacrylate, and n-octyl cyanoacrylate can be used to reduce the biological toxicity of cyanoacrylate adhesives. This discovery has promoted the further development of medical soft tissue adhesives.

At present, α-cyanoacrylate adhesives have a series of problems such as high hardness, poor toughness, repeated wear and tear causing tissue damage, premature detachment or rupture of adhesive films, and even reactive inflammatory reactions. Most seriously, its clinical application is limited due to its non-absorbability.

The absorbable medical soft tissue adhesive of the present disclosure solves the above problems, and the absorbable medical soft tissue adhesive can be cured quickly, and has good degradability and high adhesion strength.

In one embodiment, the present disclosure provides an absorbable medical soft tissue adhesive, comprising a component A and a component B:

The component A comprises a cycloketene acetal compound and an oxidizing agent;

The component B comprises a vinyl monomer, a cross-linking agent, a substance for promoting tissue and organ healing, and a reducing agent.

In the present disclosure, the molar ratio of the vinyl monomer to the cycloketene acetal compound is 0.01 to 100:1; preferably, 0.1 to 10:1.

The molar ratio of the cross-linking agent to the cycloketene acetal compound is 0.001 to 0.2:1; preferably 0.005 to 0.05:1.

The molar ratio of the substance for promoting tissue and organ healing to the cycloketene acetal compound is $1\times10^{-8}$ to $1\times10^{-4}$:1, preferably $1\times10^{-7}$ to $1\times10^{-6}$:1.

In the present disclosure, the component B of the absorbable medical soft tissue adhesive preferably further comprises an antibacterial agent; the antibacterial agent is selected from one or more of penicillins, cephalosporins, aminoglycosides, macrolides, lincomycins, quinolones, tetracyclines, sulfonamides, silver ions, zinc ions, antibacterial peptide, coumarin compound, sulfobetaines, polyguanidine polymers and benzalkonium chloride.

The molar ratio of the antibacterial agent to the cycloketene acetal compound is $1\times10^{-8}$ to $1\times10^{-4}$:1, preferably $1\times10^{-7}$ to $1\times10^{-6}$:1.

In the present disclosure, the cycloketene acetal compound is selected from one or more of 2-methylene-1,3-dioxepane (MIDO), 2-methylene-4-phenyl-1,3-dioxolane (MPDL), 5,6-benzo-2-methylene-1,3-dioxepane (BMDO) and 4,7-dimethyl-2-methylene-1,3-dioxepane (DMMDO).

The vinyl monomer is selected from one or more of (meth)acrylic acid, (meth)acrylate, vinyl acetate, maleimide polyethylene glycol carboxylic acid, biotin-PEG-6-maleimide, m-maleimidobenzoyl-N-hydroxysulfosuccinimide ester, 6-maleimidohexanoic acid, ethylene glycol vinyl ether, tetramethylene glycol monovinyl ether, vinyl (2-chloroethyl) ether, (meth)acryloyloxyphosphorylcholine, 10-(phosphonooxy)decyl methacrylate, sulfobetaine methacrylate, 4-methacryloyloxyethyl trimellitic anhydride, dopamine methacrylamide, N-acryloyl(trimethylol)aminomethane, poly(ethylene glycol) methacrylate, 2-(N,N-dimethylamino)ethyl methacrylate, (meth)allylamine and O-allylhydroxylamine.

In the present disclosure, the cross-linking agent is selected from one or more of methacrylic anhydride, diallyl maleate, bis(2-methacryloxyethyl)phosphate, tri(ethylene glycol)divinyl ether, diallylamine, triallylamine, N-methyldiallylamine, 1,5-hexadiene, diallyl disulfide and diallyldimethylsilane.

The substance for promoting the tissue and organ healing is selected from one or more of β-1,3-glucan and derivatives thereof, hyaluronic acid and asiaticoside.

In the present disclosure, the oxidizing agent is selected from one or more of benzoyl oxide, tert-butyl hydroperoxide, ammonium persulfate and hydrogen peroxide.

The reducing agent is selected from one or more of N,N-dimethyl-p-toluidine, sodium metabisulfite, sodium bisulfite and ferrous sulfate.

The oxidizing agent in the component A and the reducing agent in the component B are used as redox radical polymerization initiators.

In the present disclosure, the molar ratio of the oxidizing agent to the cycloketene acetal compound is 0.001 to 0.2:1; preferably 0.005 to 0.05:1.

The molar ratio of the oxidizing agent to the reducing agent is 0.01 to 10:1, preferably 0.2 to 2:1.

The present disclosure provides a preparation method of the absorbable medical soft tissue adhesive according to the above technical solution, comprising the following steps:

1) Mixing a cycloketene acetal compound and an oxidizing agent to obtain a component A;
Mixing a vinyl monomer, a cross-linking agent, a substance for promoting tissue and organ healing, and a reducing agent to obtain a component B;
2) Mixing the component A with the component B uniformly, and performing the polymerization reaction to obtain an absorbable medical soft tissue adhesive.

The soft tissue adhesive provided by the present disclosure has a simple preparation method and is ready-to-use, which has a convenient use process, an ideal implementation time window of 1-5 min, and strong clinical maneuverability.

In the present disclosure, the duration of the uniform mixing in the step 2) is 1-300 s, preferably 3-100 s, and more preferably 5-20 s.

In the present disclosure, after the component A and the component B are mixed, the system undergoes an in-situ free radical ring-opening polymerization reaction, during which the temperature of the polymerization reaction is 30° C. to 50° C., preferably 35° C. to 38° C. The polymerization reaction is a ring-opening polymerization reaction based on free radicals as the active center. After the radical polymerization of the components, the main chain contains a structure of ester bond.

The present disclosure provides an application of the absorbable medical soft tissue adhesive described in the above technical solution or the absorbable medical soft tissue adhesive prepared by the preparation method described in the above technical solution in the preparation of a medical adhesive.

The present disclosure also provides a method for adhesion of a wound site, comprising applying the absorbable medical soft tissue adhesive described in the above technical solution or the absorbable medical soft tissue adhesive prepared by the preparation method described in the above technical solution to the wound site.

In the present disclosure, the wound site is a wound or a surgical wound of tissue, organ or skin.

The medical soft tissue adhesive provided by the present disclosure comprises a component A and a component B. The component A and the component B are mixed, and then the mixed solution is quickly coated on a wound or a surgical incision of tissue, organ or skin, then the in-situ free radical ring-opening polymerization reaction occurs quickly to realize the rapid adhesive closure of wounds or surgical incisions. The duration of coating the mixed solution is 1-600 s, preferably 1-30 s.

Compared with the prior art, the absorbable medical soft tissue adhesive provided by the present disclosure is formed by in-situ curing of free radical ring-opening polymerization under the initiation of a redox free radical polymerization initiator in the human body environment. The reaction process is rapid, in which the adhesive cures within 20 s to 3 min, and the reaction is slightly exothermic, which will not burn the human body. After the free radical ring-opening polymerization of cycloketene acetal compound, the main chain contains a structure of ester bond, which can be degraded in a physiological environment (8-week degradation rate>20%), and has good degradability; the mild reaction conditions are conducive to the loading of the hemostatic agent and the substance for promoting the healing of tissues and organs. With the degradation of the adhesive, these substances are gradually exposed and released to promote tissue healing and avoid bacterial infection; the adhesive quickly obtains high mechanical strength and adhesion strength, wherein the adhesion strength is >160 KPa within 5 min, which is not easy to be swollen under physiological environment and has good physiological stability.

Another object of the present disclosure is to provide an absorbable bioactive bone cement, a preparation method thereof and application thereof, wherein the bone cement has both osteogenic activity and absorbability, and has characteristics of rapid curing, curing without generating much heat, high adhesion strength, no shrinking or loosening, biodegradability and other characteristics.

Bone cement is a medical material used in orthopedic surgery, which is widely used in fracture surgery fixation, joint surgery fixation and other bone injury conditions. Bone cement usually comprises solid phase powder and liquid phase components, which are mixed into a slurry in a certain ratio at room temperature and injected into the complex and irregular bone defect site to cure in situ. At present, the commonly used bone cements are mainly poly(methyl methacrylate) bone cement, calcium phosphate bone cement, calcium sulfate bone cement, etc. 1. Poly(methyl methacrylate) bone cement is a room temperature self-setting adhesive consisting of powder and liquid. Although it is widely used, it has the following shortcomings: ① It has no osteogenic activity and cannot form organic chemical interfacial bonding with the host bone tissue, which causes the long-term existence of fractures around the defect site. Although certain stability is achieved by microscopic locking and volume filling effect in a short term after surgery, with the bone resorption and other reactions at the fracture interface in the later period, the stability of long-term defect site is at risk. ② It does not degrade, resulting in that its high elastic modulus and stress concentration cannot be relieved for a long time, increasing the risk of fractures in adjacent sites, and also bringing difficulties to the treatment of degenerative diseases in adjacent sites. ③ The curing polymerization reaction generates a large amount of heat, and the heat accumulation can easily cause damage to the surrounding tissue and bone marrow. Moreover, the temperature will fall back due to the temperature difference, leading to the shrinkage of the bone cement, and causing the subsequent loosening of the joint prosthesis. 2. Calcium phosphate bone cement is a bone cement with a structure similar to human bone tissue, which is formed by adding two or more calcium phosphate powders to a liquid phase conditioner for hydrating and hardening. The disadvantages of this material are: it generally has poor injectability; low mechanical property, which makes it difficult to be applied to the load-bearing sites; and too fast degradation rate. 3. Calcium sulfate bone cement is similar to calcium phosphate bone cement, which has degradability and osteoconductivity. The disadvantages thereof are: it has long curing time, large modulus, low mechanical strength, and too fast degradation rate. Calcium phosphate bone cement and calcium sulfate bone cement have obvious shortcomings, which have little clinical application.

The absorbable bioactive bone cement of the present disclosure solves the above problems, wherein the absorbable bioactive bone cement has both osteogenic activity and absorbability, which has characteristics of rapid curing, curing without generating much heat, high adhesion strength, no shrinking or loosening, biodegradability, etc.

In one embodiment, the present disclosure provides an absorbable bioactive bone cement, comprising a component A and a component B;

The component A comprises a cycloketene acetal compound and an oxidizing agent;

The component B comprises a hydrophobic vinyl monomer, a hydrophilic cross-linking agent, and an inorganic nanomaterial-supported reducing agent.

The absorbable bioactive bone cement provided by the invention has both osteogenic activity and absorbability, no much heat generated when curing, no shrinking or loosening, which is suitable for total joint replacement, vertebroplasty, reconstruction of bone defect, and treatment of infectious disease, etc.

In the present disclosure, the cycloketene acetal compound is selected from one or more of 2-methylene-1,3-dioxepane (MDO), 2-methylene-4-phenyl-1,3-dioxolane (MPDL), 5,6-benzo-2-methylene-1,3-dioxepane (BMDO) and 4,7-dimethyl-2-methylene-1,3-dioxepane (DMMDO); FIG. 1 is the structural formula of the above-mentioned cycloketene acetal compounds.

In the present disclosure, the oxidizing agent is selected from one or more of benzoyl peroxide, tert-butyl hydroperoxide, ammonium persulfate and hydrogen peroxide.

In the present disclosure, the hydrophobic vinyl monomer is selected from one or more of acrylate, methacrylate, N-tert-butylacrylamide, N-dodecylacrylamide, 3-(methacryloyloxy)propyltrimethoxysilane and vinyl acetate; in specific embodiments, the hydrophobic vinyl monomer is 3-(methacryloyloxy)propyltrimethoxysilane, methyl methacrylate, N-tert-butylacrylamide or vinyl acetate.

In the present disclosure, the hydrophilic cross-linking agent is a monomer containing two or more vinyl units; the hydrophilic cross-linking agent is selected from one or more of poly(ethylene glycol) dimethacrylate, polyethylene glycol diacrylate, diacrylamide polyethylene glycol, dimethacrylamide polyethylene glycol, phosphate dimethacrylate and phosphate diacrylate. In a specific embodiment, the hydrophilic cross-linking agent is selected from poly(ethylene glycol) dimethacrylate.

In the present disclosure, the reducing agent in the inorganic nanomaterial-supported reducing agent is selected from one or more of N,N-dimethyl-p-toluidine, sodium metabisulfite, sodium bisulfite and ferrous sulfate. The inorganic nanomaterial in the inorganic nanomaterial-supported reducing agent is selected from one or more of nano-hydroxyapatite, nano-calcium triphosphate and nano-bioactive glass.

In specific embodiments, the inorganic nanomaterial-supported reducing agent is N,N'-dimethyl-p-toluidine supported by bioactive glass, N,N'-dimethyl-p-toluidine supported by β-tricalcium phosphate, or N,N'-dimethyl-p-toluidine supported by nano-hydroxyapatite.

In the present disclosure, the molar ratio of the hydrophobic vinyl monomer to the cycloketene acetal compound is 0.01 to 100:1, preferably 0.1 to 10:1;

The molar ratio of the hydrophilic cross-linking agent to the cycloketene acetal compound is 0.001 to 0.2:1, preferably 0.005 to 0.05:1.

In the present disclosure, the molar ratio of the oxidizing agent to the cycloketene acetal compound is 0.001 to 0.2:1; preferably 0.002 to 0.02:1.

The molar ratio of the oxidizing agent to the reducing agent is 0.01 to 10:1, preferably 0.2 to 2:1.

The ratio of the mass of the inorganic nanomaterial to the total mass of the hydrophobic vinyl monomer and the cycloketene acetal compound is 0.001 to 100:1; preferably 0.1 to 0.5:1;

The present disclosure provides a preparation method of the absorbable bioactive bone adhesive according to the above technical solution, comprising the following steps:

Dissolving an oxidizing agent in a cycloketene acetal compound to obtain a mixed solution A;

Mixing a hydrophobic vinyl monomer, a hydrophilic cross-linking agent and an inorganic nanomaterial-supported reducing agent uniformly to obtain a mixed solution B;

Mixing the mixed solution A with the mixed solution B evenly, and performing in-situ curing to obtain an absorbable bioactive bone adhesive.

In the present disclosure, the oxidizing agent in the component A and the inorganic nanomaterial-supported reducing agent in the component B are used as redox radical polymerization initiators; the in-situ curing is namely performing ring-opening polymerization reaction; the ring-opening polymerization reaction is carried out under the initiation of the redox radical polymerization initiator, based on free radicals as the active center; after the radical polymerization of the components, the main chain contains a structure of ester bond.

The present disclosure provides an application of the absorbable bioactive bone cement described in the above technical solution or the absorbable bioactive bone cement prepared by the preparation method described in the above technical solution in the preparation of bone cement products.

The present disclosure also provides a method for treating a bone injury site, which comprises applying the absorbable bioactive bone cement described in the above technical solution or the absorbable bioactive bone cement prepared by the preparation method described in the above technical solution to the bone injury site.

In the present disclosure, the bone cement is filled to the bone injury site at dough phase.

The filling is performed in any of treatments including total joint replacement, vertebroplasty, reconstruction of bone defect, and treatment of infectious disease.

The dough phase is a stage that occurs during the polymerization of monomers and polymers. At this time, there is no excess monomer in the system, the stickiness disappears, and the system is in the form of a plastic dough. At this time, the polymerization reaction speed is accelerated, and heat generation begins. The bone cement should be placed between the bone surface and the artificial prosthesis as soon as possible for bonding. The time when the dough phase appears is also affected by the room temperature. The higher the room temperature is, the faster it is. The lower the room temperature is, the slower it is.

The present disclosure provides an absorbable bioactive bone cement, comprising a component A and a component B; the component A comprises a cycloketene acetal compound and an oxidizing agent; the component B comprises a hydrophobic vinyl monomer, a hydrophilic cross-linking agent, and an inorganic nanomaterial-supported reducing agent. The bone cement provided by the present disclosure is formed by in-situ curing of free radical ring-opening polymerization reaction in the human body environment, the reaction process thereof is rapid, the reaction is slightly exothermic and will not burn the human body, and the subsequent use will not cause loosening. The added inorganic nanomaterial has osteogenic activity and can be absorbed by the human body, which can be degraded and absorbed with free radical ring-opening polymer of cycloketene acetal compound in a physiological environment. However, the absorption time of the inorganic nanomaterial is longer, avoiding the deficiency of too short degradation time of the calcium phosphate bone cement and calcium sulfate bone cement, which is suitable for total joint replacement, vertebroplasty, reconstruction of bone defect, treatment of infectious diseases, etc.

Unless otherwise defined, terms used herein have the same meaning as commonly understood by those of ordinary skill in the art. The terms used in the specification are used to describe specific embodiments only and are not intended to limit the present disclosure.

DETAILED DESCRIPTION

Figure 1:
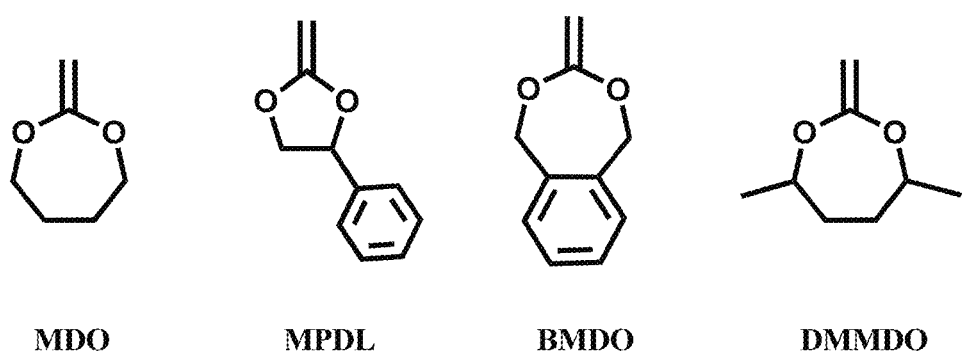
FIG. 1 is the structural formula of cycloketene acetal compounds in the present disclosure.

In order to further illustrate the present disclosure, the medical adhesive and the preparation method thereof provided by the present disclosure are described in detail below with reference to the embodiments, but they should not be construed as limiting the protection scope of the present disclosure.

Preliminary Example 1.1 Synthesis of MDO Monomer 2-bromo-1,1'-dimethoxyethane (65 g, 0.4 mol), 1,4-butanediol (36 g, 0.51 mol) and Dowex 50 acidic ion exchange resin (0.5 g) were added to a reaction flask, in which the reaction temperature was set to 115° C. During the reaction process, the by-product methanol was continuously collected using a water separator, to evaluate the reaction progress according to the amount of the collected methanol. The reaction lasted for about 4 hours. After the reaction was completed, the acidic resin was removed by filtration. The obtained crude product was subjected to vacuum distillation to collect the fraction at 95° C. The product obtained above (35 g, 0.18 mol) was dissolved in 70 ml of dry tetrahydrofuran and placed in a reaction flask, then added with Aliquat 336 (1.67 g, 0.004 mol), as the reaction temperature was reduced to 0° C., gradually added with t-BuOK (40.41 g, 0.36 mol), and the temperature was maintained to react for 2 h. After the reaction was completed, the solid was removed by filtration, and the organic phase was concentrated to obtain a crude product, which was then distilled to collect the fraction at 25° C., namely the product MDO.

Preliminary Example 1.2

Preparation Process of Cycloketene Acetal Unit MPDL:
2-bromo-1,1'-dimethoxyethane (65 g, 0.4 mol), 1-phenyl-1,2-ethylene glycol (69 g, 0.5 mol) and Dowex 50 acidic ion exchange resin (0.5 g) were added into a reaction flask, in which the reaction temperature was set to 120° C. During the reaction process, the by-product methanol was continuously collected using a water separator, to evaluate the reaction progress according to the amount of the collected methanol. The reaction lasted for about 4 hours. After the reaction was completed, the acidic resin was removed by filtration. The obtained crude product was subjected to vacuum distillation to collect the fraction around 70° C.; then added with Aliquat 336 (1.67 g, 0.004 mol), as the reaction temperature was reduced to 0° C., gradually added with t-BuOK (40.41 g, 0.36 mol), and the temperature was maintained to react for 2 h. After the reaction was completed, the solid was removed by filtration, and the organic phase was concentrated to obtain a crude product, which was then distilled to collect the fraction at 50° C., namely the product MPDL.

Example 1.1

A cycloketene acetal unit MDO and an oxidizing agent benzoyl peroxide (BPO, 2 mol %) were mixed uniformly to form a mixed solution A; a co-monomer methacrylic acid (MAA), a cross-linking agent ethylene glycol dimethacrylate (1 wt %) and a reducing agent N,N'-dimethyl-p-toluidine (DMPT, 2 mol %) were mixed uniformly to form a mixed solution B, wherein the molar ratio of MDO to IAA was 2:1, 1:1 and 1:1 and 1:2, respectively; the mixed solution A and B were quickly mixed and evenly coated on an animal bone plate, which was covered with another bone plate and slightly pressed for 1-2 minutes to realize free radical ring-opening polymerization at room temperature to achieve bone adhesion, so as to obtain an in vitro bone bonded part.

Example 1.2

A cycloketene acetal unit MDO and an oxidizing agent benzoyl peroxide (BPO, 2 mol %) were mixed uniformly to form a mixed solution A; a co-monomer 10-(phosphonooxy)decyl methacrylate (MDP), a cross-linking agent ethylene glycol dimethacrylate (1 wt %) and a reducing agent N,N'-dimethyl-p-toluidine (DMPT, 2 mol %) were mixed uniformly to form a mixed solution B, wherein the molar ratio of MDO to MDP was 2:1, 1:1 and 1:2, respectively; the mixed solution A and B were quickly mixed and evenly coated on an animal bone plate, which was covered with another bone plate and slightly pressed for 1-2 minutes to realize free radical ring-opening polymerization at room temperature to achieve bone adhesion, so as to obtain an in vitro bone bonded part.

Example 1.3

A cycloketene acetal unit MPDL and an oxidizing agent benzoyl peroxide (BPO, 2 mol %) were mixed uniformly to form a mixed solution A; a co-monomer methacrylic acid (MAA), a cross-linking agent ethylene glycol dimethacrylate (1 wt %) and a reducing agent N,N'-dimethyl-p-toluidine (DMPT, 2 mol %) were mixed uniformly to form a mixed solution B, wherein the molar ratio of MPDL to IAA was 2:1, 1:1 and 1:2, respectively; the mixed solution A and B were quickly mixed and evenly coated on an animal bone plate, which was covered with another bone plate and slightly pressed for 1 to 2 minutes to realize free radical ring-opening polymerization at room temperature to achieve bone adhesion, so as to obtain an in vitro bone bonded part.

Example 1.4

A cycloketene acetal unit MPDL and an oxidizing agent benzoyl peroxide (BPO, 2 mol %) were mixed uniformly to form a mixed solution A; a co-monomer 10-(phosphonooxy)decyl methacrylate (MDP), a cross-linking agent ethylene glycol dimethacrylate (1 wt %) and a reducing agent N,N'-dimethyl-p-toluidine (DMPT, 2 mol %) were mixed uniformly to form a mixed solution B, wherein the molar ratio of MPDL to MDP was 2:1, 1:1 and 1:2, respectively; the mixed solution A and B were quickly mixed and evenly coated on an animal bone plate, which was covered with another bone plate and slightly pressed for 1 to 2 minutes to realize free radical ring-opening polymerization at room temperature to achieve bone adhesion, so as to obtain an in vitro bone bonded part.

Comparative Example 1.1

A mixed solution of 1 g of 2-octyl cyanoacrylate (OCA) and 0.5 mg of p-toluenesulfonic acid (PTSA, stabilizer) was quickly and evenly coated on an animal bone plate, which was covered with another bone plate and slightly pressed for 1 to 2 min to realize free radical ring-opening polymerization at room temperature to achieve bone adhesion, so as to obtain an in vitro bone bonded part.

Comparative Example 1.2

Poly(methyl methacrylate) powder (PMMA, average molecular weight of 8000, particle shape) and benzoyl peroxide (BPO, 1 wt %) were mixed uniformly to form a solid component. On the other hand, the methyl methacrylate monomer (MMA) and N,N'-dimethyl-p-toluidine (DMPT, 1 wt %) were mixed uniformly to form a liquid component. The solid and liquid components prepared above were mixed evenly in a mass ratio of 3:1, forming a viscous liquid state, which was quickly coated on an animal bone plate, covered with another bone plate and pressed slightly for 1 to 2 minutes to realize free radical ring-opening polymerization at room temperature to achieve bone adhesion, so as to obtain an in vitro bone bonded part.

Time of In-Situ Curing

Preferably in Example 1.1, a cycloketene acetal unit MDO and an oxidizing agent benzoyl peroxide (BPO, 2 mol %) were mixed uniformly to form a mixed solution A; a co-monomer methacrylic acid (MAA), a cross-linking agent ethylene glycol dimethacrylate (1 wt %) and a reducing agent N,N'-dimethyl-p-toluidine (DMPT, 2 mol %) were mixed uniformly to form a mixed solution B, wherein the molar ratio of MDO to MAA was 2:1, 1:1 and 1:2, respectively. The mixed solution A and mixed solution B were mixed quickly and evenly to evaluate the time of curing of the mixed solution at room temperature by observing the flow state of the mixed solution through inverting the centrifuge tube.

Figure 2:
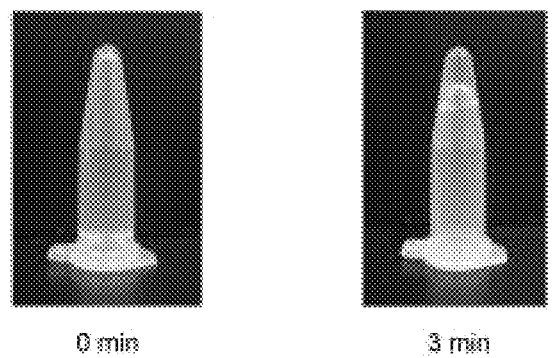
FIG. 2 is the diagram of the in-situ curing time test in the present disclosure.

Time of the Curing is Shown in FIG. 2.

As shown in FIG. 2: When the initiator was added, the whole mixed solution was in a flowing state. With the extension of time, the monomer mixed solution underwent in-situ polymerization at room temperature, which was cured within 3 min and converted into a non-flowing state. The curing process was fast, reducing the operation time and facilitating the clinical application.

In Vitro Bone Adhesion Experiment

Figure 3:
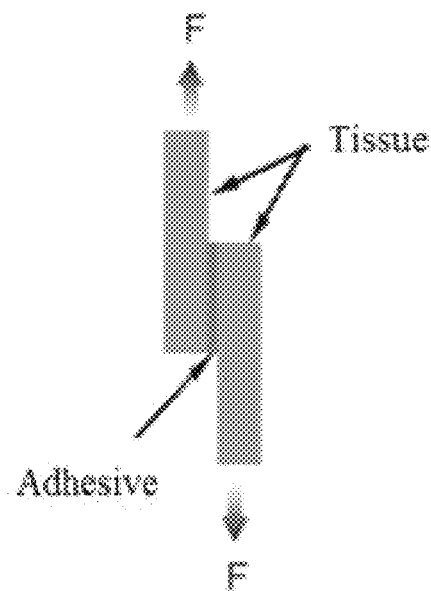
FIG. 3 is the schematic diagram of the shear adhesion test model of the in vitro bone adhesion experiment in the present disclosure.

According to GB/T 7124-2008 standard, the in vitro bone tissue adhesion strength was obtained by shear adhesion test, and the shear adhesion model is shown in FIG. 3. Before the experiment, bovine bones were selected and cut into regular plate-like splines, which had a length and width of 10 cm×2.5 cm, and a thickness of 0.2 cm. The preparation of in vitro bone bonded part was as described in Examples 1.1 to 1.4 and Comparative examples 1.1 to 1.2, wherein the adhesion area of the bone bonded part was 2.5 cm×1.0 cm; the obtained bone bonded part was placed at room temperature for 2 h and then subjected to a tensile test, which was carried out on a universal testing machine (LD-5 type of LLOYD company, sensor 2.5 kN), wherein the tensile rate was 5 mm/min. The shear adhesion strength was calculated by dividing the load force at the fracture of the bone bonded part by the adhesion area.

TABLE 1.1

In vitro bone tissue adhesion strength (MPa)

| Cycloketene acetal:co-monomer (mol:mol) | Example 1.1 | Example 1.2 | Example 1.3 | Example 1.4 | Comparative example 1.1 | Comparative example 1.2 |
|---|---|---|---|---|---|---|
| 2:1 | 1.8 ± 0.3 | 2.4 ± 0.5 | 1.9 ± 0.2 | 2.1 ± 0.1 | 4.6 ± 0.2 | 1.1 ± 0.1 |
| 1:1 | 3.3 ± 0.4 | 3.7 ± 0.3 | 3.1 ± 0.1 | 3.4 ± 0.2 | | |
| 1:2 | 4.9 ± 0.2 | 5.4 ± 0.1 | 4.4 ± 0.1 | 4.5 ± 0.1 | | |

The results of the in vitro bone adhesion test are shown in Table 1.1.

Figure 4:
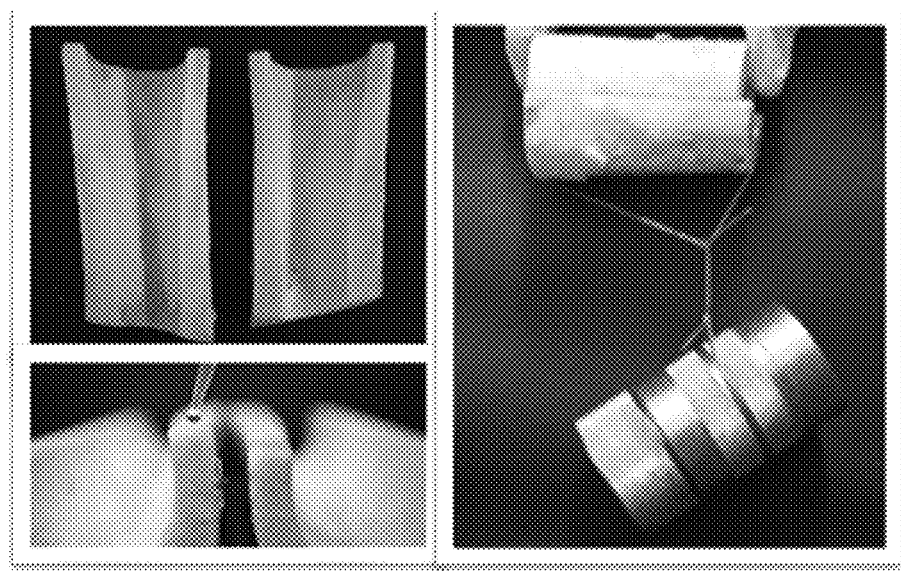
FIG. 4 is the adhesion test of the strong bone adhesive prepared in Example 1.1 of the present disclosure to the bovine stick bone.

As shown in Table 1.1: the bone adhesion strength of the materials in Examples 1.1 to 1.4 was all above 1 MPa, showing good bone adhesion performance. It can be seen from FIG. 4 that these materials had good adhesion performance to bovine stick bones. It can be seen that with the increase of the proportion of co-monomers, the bone adhesion strength of the materials gradually increased, this is because the co-monomers in Example 1.1 and Example 1.3 were methacrylic acid, the introduction of which could improve the polarity and hydrophilicity of the material, improving the contact and infiltration to the bone tissue. While the co-monomers in Example 1.2 and Example 1.4 were 10-(phosphonooxy)decyl methacrylate, in the structure of which the phosphate group can achieve covalent binding with bone tissue, so that it had higher adhesion strength. In addition, it can be seen that through the adjustment of the ratio, the bone adhesion strength of the Examples was higher than that of the cyanoacrylate monomers in Comparative example 1.1; the poly(methyl methacrylate) in Comparative example 1.2 was usually used as a bone filling material (such as bone cement), and its bone adhesion strength was low, only about 1.1 MPa.

In Vivo Degradation Assay

Balb/c mice (20 g, female) were shaved off back hairs in a sterile environment, whose skins were cleaned, then placed in an isoflurane-containing anesthesia box for anesthesia, fixed on an operating table, and maintained under anesthesia with a breathing mask. The dorsal skin of mice was sterilized with iodophor, and cut out an opening (about 1 cm) with a scalpel, and the fascia between the skin and muscle was separated with scissors and forceps to form a small pocket. The cured samples in Comparative examples 1.1 to 1.2 and Examples 1.1 to 1.4 were made into a size of 0.5 cm×0.5 cm, and implanted under the dorsal skin of mice. The tissue was sutured, and disinfected with iodophor again. 6 mice were randomly implanted in each case. After fed for 8 weeks, the mice were euthanized. The samples of Examples 1.1 to 1.4 and Comparative examples 1.1 to 1.2 were taken out to observe the morphology of the samples, and to weigh the weight of the samples. The degradation rate was calculated by comparing with the samples before implanted.

Figure 5:
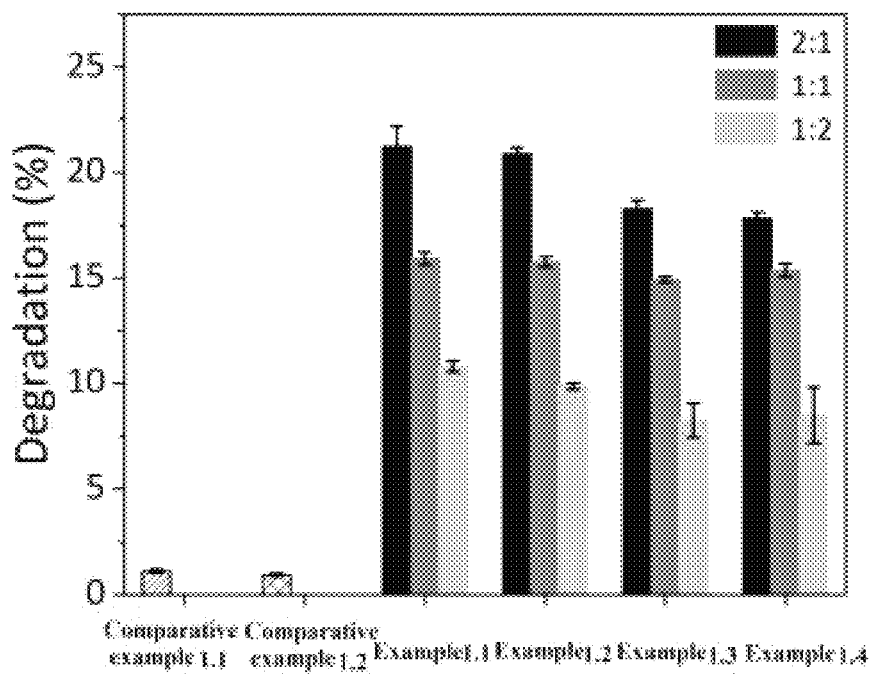
FIG. 5 is the diagram of the in vivo degradation test of the materials in Comparative examples 1.1 to 1.2 and Examples 1.1 to 1.4 of the present disclosure.

The in vivo degradation test of the materials in Comparative examples 1.1 to 1.2 and Examples 1.1 to 1.4 is shown in FIG. 5.

As shown in FIG. 5: the materials in Examples 1.1 to 1.4 all showed good degradation rates after being maintained in a physiological environment for 8 weeks. In Example 1.1, when MDO:MAA was 2:1, the material had the highest degradation rate, reaching 21.2%; the larger the proportion of MDO was, the more obvious the degree of degradation of the material was, indicating that the introduction of MDO ring-opening polymer provided good degradability for the material. In addition, the degradation rates of the materials in Comparative example 1.1 and Comparative example 1.2 for 8 weeks were 1.1% and 0.91%, respectively, which showed that the degradability of the material was poor, far lower than that in Examples 1.1 to 1.4, indicating that the bone tissue adhesive material constructed by the present disclosure had excellent degradability in vivo.

In order to further illustrate that the above-mentioned fast-curing and degradable strong bone adhesive can simultaneously promote bone regeneration, a fast-curing and degradable strong bone adhesive with osteogenic activity and a preparation method thereof provided by the present disclosure are described in detail below with reference to examples, but they should not be construed as limiting the protection scope of the present disclosure.

Comparative Example 1.3

A cycloketene acetal unit MDO and an oxidizing agent benzoyl peroxide (BPO, 2 mol %) were mixed uniformly to form a mixed solution A; a co-monomer 10-(phosphonooxy)decyl methacrylate (MDP), a cross-linking agent bis(2-methacryloxyethyl)phosphate (1 wt %), and a reducing agent N,N'-dimethyl-p-toluidine (DMPT, 2 mol %) were mixed uniformly to form a mixed solution B, wherein the molar ratio of MDO to MDP was 2:1, 1:1 and 1:2, respectively. The mixed solution A and B were quickly mixed and evenly coated on an animal bone plate, which was covered with another bone plate and slightly pressed for 1 to 2 minutes to realize free radical ring-opening polymerization at room temperature to achieve bone adhesion, so as to obtain an in vitro bone bonded part.

Example 1.5

A cycloketene acetal unit MDO and an oxidizing agent benzoyl peroxide (BPO, 2 mol %) were mixed uniformly to form a mixed solution A; a co-monomer methacrylic acid (MAA), a cross-linking agent bis(2-methacryloxyethyl) phosphate (1 wt %), a bioactive ingredient β-tricalcium phosphate (10 wt %) and a reducing agent N,N'-dimethyl-p-toluidine (DMPT, 2 mol %) were mixed uniformly to form a mixed solution B, wherein the molar ratio of MDO to MAA was 2:1, 1:1 and 1:2, respectively. The mixed solution A and B were quickly mixed and evenly coated on an animal bone plate, which was covered with another bone plate and slightly pressed for 1 to 2 minutes to realize free radical ring-opening polymerization at room temperature to achieve bone adhesion, so as to obtain an in vitro bone bonded part.

Example 1.6

A cycloketene acetal unit MDO and an oxidizing agent benzoyl peroxide (BPO, 2 mol %) were mixed uniformly to form a mixed solution A; a co-monomer 10-(phosphonooxy) decyl methacrylate (MDP), a cross-linking agent bis(2-methacryloxyethyl)phosphate (1 wt %), a bioactive ingredient 45S5 bioactive glass (10 wt %) and a reducing agent N,N'-dimethyl-p-toluidine (DMPT, 2 mol %) were mixed uniformly to form a mixed solution B, wherein the molar ratio of MDO to MDP was 2:1, 1:1 and 1:2, respectively. The mixed solution A and B were quickly mixed and evenly coated on an animal bone plate, which was covered with another bone plate and slightly pressed for 1 to 2 minutes to realize free radical ring-opening polymerization at room temperature to achieve bone adhesion, so as to obtain an in vitro bone bonded part.

Example 1.7

A cycloketene acetal unit MDO and an oxidizing agent benzoyl peroxide (BPO, 2 mol %) were mixed uniformly to form a mixed solution A; a co-monomer methacrylic acid (MAA), a cross-linking agent bis(2-methacryloxyethyl) phosphate (1 wt %), dexamethasone (10 wt %) and a reducing agent N,N'-dimethyl-p-toluidine (DMPT, 2 mol %) were mixed uniformly to form a mixed solution B, wherein the molar ratio of MDO to MAA was 2:1, 1:1 and 1:2, respectively. The mixed solution A and B were quickly mixed and evenly coated on an animal bone plate, which was covered with another bone plate and slightly pressed for 1 to 2 minutes to realize free radical ring-opening polymerization at room temperature to achieve bone adhesion, so as to obtain an in vitro bone bonded part.

Example 1.8

A cycloketene acetal unit MDO and an oxidizing agent benzoyl peroxide (BPO, 2 mol %) were mixed uniformly to form a mixed solution A; a co-monomer 10-(phosphonooxy) decyl methacrylate (MDP), a cross-linking agent bis(2-methacryloxyethyl)phosphate (1 wt %), BMP-2 (10 wt %) and a reducing agent N,N'-dimethyl-p-toluidine (DMPT, 2 mol %) were mixed uniformly to form a mixed solution B, wherein the molar ratio of MDO to MDP was 2:1, 1:1 and 1:2, respectively; the mixed solution A and B were quickly mixed and evenly coated on an animal bone plate, which was covered with another bone plate and slightly pressed for 1 to 2 minutes to realize free radical ring-opening polymerization at room temperature to achieve bone adhesion, so as to obtain an in vitro bone bonded part.

In Vitro Bone Adhesion Experiment

According to GB/T 7124-2008 standard, the in vitro bone tissue adhesion strength was obtained by shear adhesion test, and the shear adhesion model is shown in FIG. 3. Before the experiment, bovine bones were selected and cut into regular plate-like splines, which had a length and width of 10 cm×2.5 cm, and a thickness of 0.2 cm. The preparation of in vitro bone bonded part was as described in Examples 1.5 to 1.8 and Comparative examples 1.3, wherein the adhesion area of the bone bonded part was 2.5 cm×1.0 cm. The obtained bone bonded part was placed at room temperature for 2 h and then subjected to a tensile test, which was carried out on a universal testing machine (LD-5 type of LLOYD company, sensor 2.5 kN), wherein the tensile rate was 5 mm/min. The shear adhesion strength was calculated by dividing the load force at the fracture of the bone bonded part by the adhesion area.

TABLE 1.2

| | In vitro bone tissue adhesion strength (MPa) | | | | | |
|---|---|---|---|---|---|---|
| Cycloketene:co-monomer (mol:mol) | Comparative example 1.1 | Comparative example 1.3 | Example 1.5 | Example 1.6 | Example 1.7 | Example 1.8 |
| 2:1 | 4.6 ± 0.2 | 2.2 ± 0.1 | 3.8 ± 0.1 | 4.1 ± 0.3 | 3.5 ± 0.2 | 3.4 ± 0.1 |
| 1:1 | | 3.5 ± 0.1 | 4.4 ± 0.3 | 4.8 ± 0.2 | 3.9 ± 0.1 | 3.8 ± 0.2 |
| 1:2 | | 3.7 ± 0.3 | 4.6 ± 0.2 | 5.1 ± 0.1 | 4.0 ± 0.2 | 3.9 ± 0.1 |

The results of in vitro bone adhesion tests are shown in Table 1.2.

As shown in Table 1.2: the bone adhesion strength of the materials in Examples 1.5 to 1.8 was all above 2 MPa, wherein the maximum adhesion strength was greater than that of Comparative example 1.1, showing good bone adhesion performance. It can be seen that with the increase of the proportion of co-monomers, the bone adhesion strength of the materials gradually increased, this is because the preferred co-monomer 10-(phosphonooxy)decyl methacrylate can improve the polarity and hydrophilicity of the material, improving the contact and infiltration to the bone tissue, and the phosphate group in its structure can achieve covalent binding with bone tissue, so it has high adhesion strength. In addition, it can be seen that the adhesion strength of Example 1.5, Example 1.6 was higher than that of Example 1.7, Example 1.8, and also Comparative example 1.3, this is because the preferred osteogenic active ingredients β-hydroxyapatite and bioactive glass had an effect of molecular chain reinforcement in the copolymer, which can improve the mechanical strength of the material, thereby improving the adhesion strength.

In Vitro Cytocompatibility Assay

According to the requirements of the cytotoxicity test in GB/T16886 "Biological Evaluation of Medical Devices", MC3T3E1 was selected as the test cell line, and the cured samples in Examples 5 to 8 were prepared and shaped into a sample size of 0.5 cm×0.5 cm. After sterilized, the samples were placed in the culture medium to prepare the sample extract, 5 extract samples were prepared in each group, and the sample medium extract was used to culture L929 cell under a condition of 37° C. and 5% $CO_2$ for 24 h. The cell viability was detected by CCK8 method, and the average of results of each group was taken.

Figure 6:
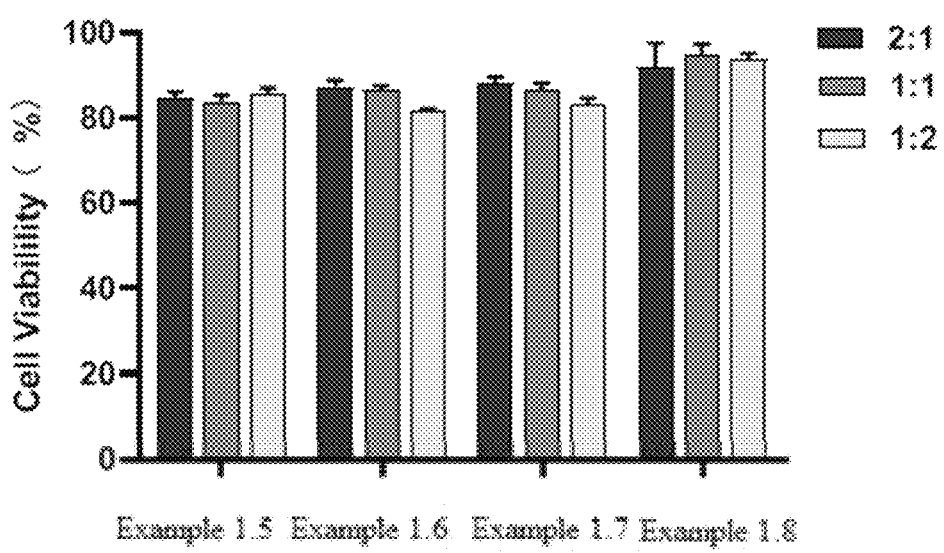
FIG. 6 is the cytocompatibility test diagram of the materials in Examples 1.5 to 1.8 of the present disclosure.

Cytocompatibility test of the materials in Example 1.5 to Example 1.8 is shown in FIG. 6.

As shown in FIG. 6: the materials in Example 1.5 to Example 1.8 all showed good cell compatibility, wherein the cell viability was all above 80%.

In Vivo Degradation Assay

Balb/c mice (20 g, female) were shaved off back hairs in a sterile environment, whose skins were cleaned, then placed in an isoflurane-containing anesthesia box for anesthesia, fixed on an operating table, and maintained under anesthesia with a breathing mask. The dorsal skin of mice was sterilized with iodophor, and cut out an opening (about 1 cm) with a scalpel, and the fascia between the skin and muscle was separated with scissors and forceps to form a small pocket. The cured samples in Comparative example 1.1, Comparative example 1.3 and Examples 1.5 to 1.8 were made into a size of 0.5 cm×0.5 cm, and implanted under the dorsal skin of mice. The tissue was sutured, and disinfected with iodophor again. 6 mice were randomly implanted in each case. After fed for 8 weeks, the mice were euthanized. The samples of Comparative example 1.1, Comparative example 1.3 and Example 1.5 to Example 1.8 were taken out to observe the morphology of the samples, and to weigh the weight of the samples. The degradation rate was calculated by comparing with the samples before implanted.

Figure 7:
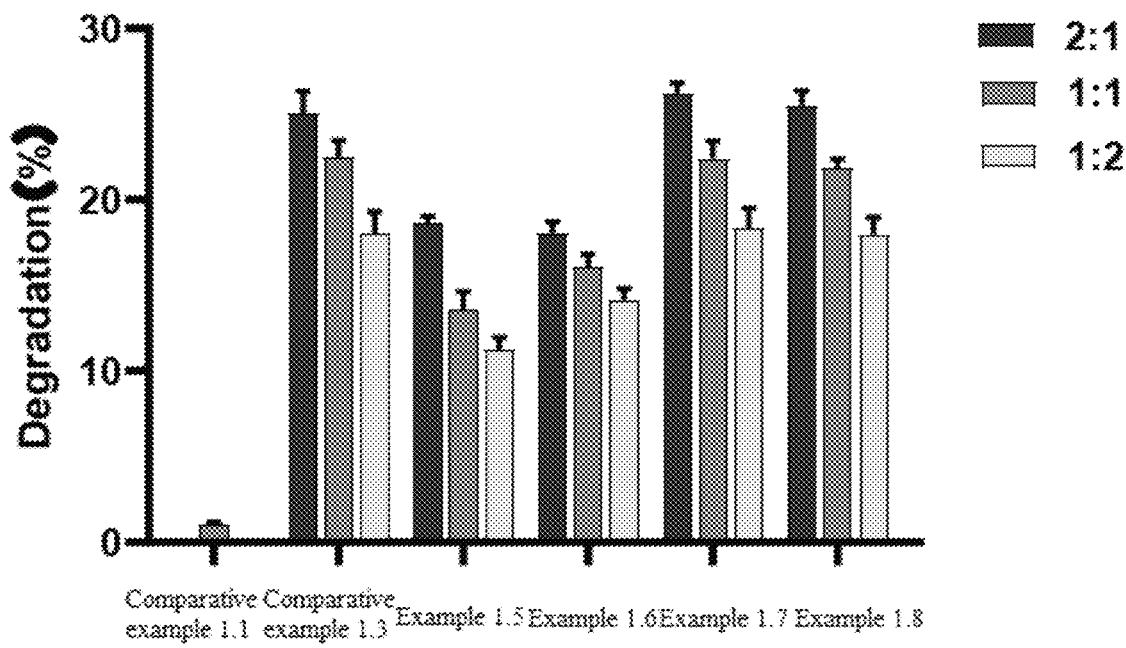
FIG. 7 is the in vivo degradation test diagram of the materials in Comparative examples 1.3 to 1.4 and Examples 1.5 to 1.8 of the present disclosure.

The in vivo degradation test of the materials in Comparative example 1.1 and Comparative example 1.3 and Examples 1.5 to 1.8 is shown in FIG. 7.

As shown in FIG. 7: the materials in Examples 1.5 to 1.8 all showed good degradation rates after being maintained in a physiological environment for 8 weeks, among which the degradation of the materials in Example 1.7, Example 1.8 and Comparative example 1.4 was the most obvious, wherein the maximum degradation rate was 25.5%. With the increase of the proportion of MDO, the degradation degree of the material was more obvious, indicating that the introduction of MDO ring-opening polymer provided good degradability for the material. In addition, the degradation rate of the material in Comparative example 1.1 for 8 weeks was 1.10%, which showed that the degradability of the material was poor, much lower than that in Examples 1.5 to 1.8, indicating that the bone tissue adhesive material constructed by the present disclosure had excellent degradability in vivo.

Osteogenic Activity Assay

Figure 8:
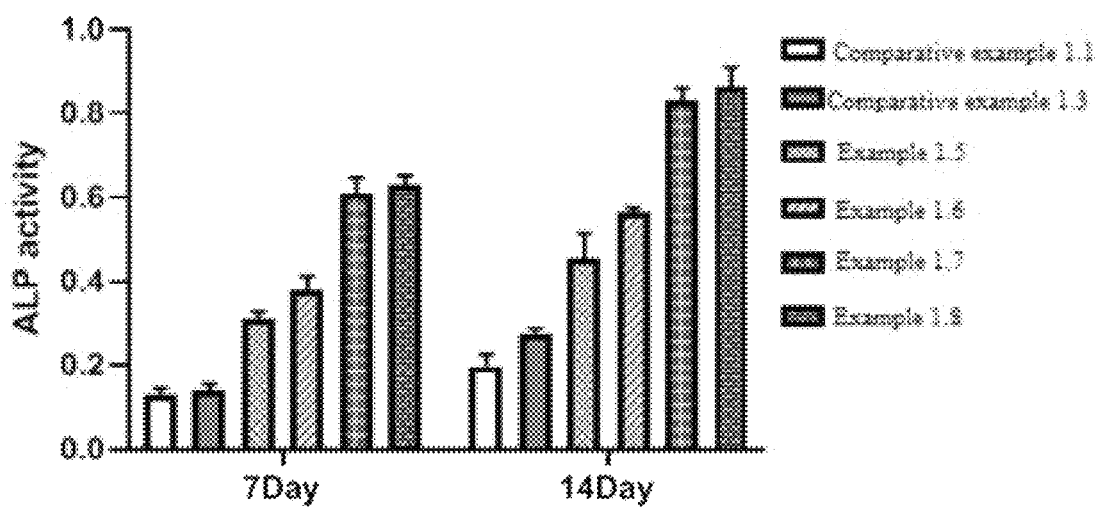
FIG. 8 is the ALP activity test in Comparative examples 1.3 to 1.4 and Examples 1.5 to 1.8 of the present disclosure.

ALP activity detection: After the osteoblast MC3T3E1 was cultured in the prefabricated samples in Examples 1.5 to 1.8 and comparative examples 1.1 and 1.3 for 7 days and 14 days, respectively, and then the old medium was removed. The cells were washed with PBS for 1 to 3 times, and then added with RIAP cell lysate. After the cells were fully lysed, the cell lysate was centrifuged to take the supernatant, and the ALP activity of the cells was detected according to the instructions of the AKP/ALP kit. FIG. 8 is the ALP activity detection diagram of the Comparative examples 1.1, 1.3 and Examples 1.5 to 1.8 of the present disclosure. It can be seen from FIG. 8 that the ALP activity of osteoblasts in Examples 1.5 to 1.8 was significantly higher than that in Examples 1.1 and 1.3. In particular, ALP activity was most significantly up-regulated in Example 1.7 and Example 1.8, representing a higher level of osteogenic differentiation of cells. In addition, with the prolongation of time (after 14 days), the ALP activity was further increased, showing a time dependence.

It can be seen from the above examples that the present disclosure provides a fast-curing and degradable strong bone adhesive and a preparation method thereof, which are used for fast adhesion of fractures, especially comminuted fractures. The bone adhesive comprises a cycloketene acetal compound, a co-monomer and a cross-linking agent, during use of which, a highly active redox initiating system is added, and the bone adhesive is coated on the bone tissue section to undergo the in-situ free radical ring-opening polymerization to achieve rapid adhesion of bone sections. The bone adhesive has a simple preparation method and is ready-to-use, which has the advantages of fast bone adhesion, high adhesion strength, biodegradability, no immune rejection, good biocompatibility, etc., and is suitable for fractures, especially in the field of clinical treatment of adhesion and regeneration and repair of bone tissue such as comminuted fractures and the like.

Example 2.1

2,5-hexanediol (1.2 g, 10.2 mmol) was dissolved in dichloromethane (170 ml) and pyridine (7.5 ml, 91.5 mmol), the reaction system was placed at −20° C. and replaced with argon, and then added dropwise with a solution of triphosgene (4.55 g, 15.2 mmol) in dichloromethane (90 ml). After the addition was completed, the mixture was returned to room temperature to react for 20 min. Then the reaction was quenched using a saturated ammonium chloride solution (100 ml), and the product mixed solution was extracted with dichloromethane to obtain the organic phase, which was washed with saturated brine, dried over anhydrous sodium sulfate, filtered, removed off solvent in vacuum, and distilled under reduced pressure to collect the fraction around 95° C. The product obtained above (0.023 g, 0.16 mmol) was dissolved in tetrahydrofuran/toluene (1:1) mixed solvent, and added with Petasis reagent (2 ml, 0.5 mmol, a tetrahydrofuran/toluene mixed solution with a concentration of 5 wt %), the reaction system was replaced with argon to react at 60 to 65° C. in the dark for 20 h. After the reaction was completed, n-hexane (10 ml) was added to form a yellow precipitate. After filtration, the filtrate was concentrated to obtain a product DMMDO.

0.1 mol cycloketene compound DMMDO was mixed with benzoyl peroxide (BPO, 2 mol %) to obtain a component A; 0.2 mol co-monomer methacrylic acid (MA) and 0.05 mol % cross-linking agent bis(2-methacryloxyethyl)phosphate, $1×10^{-5}$ mol % halloysite, $1×10^{-5}$ mol % benzalkonium chloride and N,N'-dimethyl-p-toluidine (DMPT, 2 mol %), were mixed evenly to form a component B for standby use. The component A and component B were quickly and uniformly mixed, and the obtained mixed solution was quickly and uniformly coated on the application site or in the polytetrafluoroethylene mold to undergo free radical ring-opening polymerization adhesion at room temperature.

Example 2.2

2-bromo-1,1'-dimethoxyethane (65 g, 0.4 mol), 1,4-butanediol (36 g, 0.51 mol) and Dowex 50 acidic ion exchange resin (0.5 g) were added to a reaction flask, in which the reaction temperature was set to 115° C. During the reaction process, the by-product methanol was continuously collected using a water separator, to evaluate the reaction progress according to the amount of the collected methanol. The reaction lasted for about 4 hours. After the reaction was completed, the acidic resin was removed by filtration. The obtained crude product was subjected to vacuum distillation to collect the fractions at 95° C. The product obtained above (35 g, 0.18 mol) was dissolved in 70 ml of dry tetrahydrofuran and placed in a reaction flask, then added with Aliquat 336 (1.67 g, 0.004 mol), as the reaction temperature was reduced to 0° C., gradually added with t-BuOK (40.41 g, 0.36 mol), and the temperature was maintained to react for 2 h. After the reaction was completed, the solid was removed by filtration, and the organic phase was concentrated to obtain a crude product, which was then distilled to collect the fraction at 25° C., namely the product MDO.

0.1 mol cycloketene compound MDO was mixed with benzoyl peroxide (BPO, 2 mol %) to obtain a component A; 0.02 mol co-monomer poly(ethylene glycol) methacrylate (PEM) and 0.04 mol % cross-linking agent bis(2-methacryloxyethyl)phosphate, $5 \times 10^{-6}$ mol % haemocoagulase, $1 \times 10^{-6}$ mol % polyhexamethylene biguanide hydrochloride and N,N'-dimethyl-p-toluidine (DMPT, 2 mol %), were mixed evenly to form a component B for standby use. The component A and component B were quickly and uniformly mixed, and the obtained mixed solution was quickly and uniformly coated on the application site to undergo free radical ring-opening polymerization adhesion at room temperature.

Example 2.3

2-bromo-1,1'-dimethoxyethane (65 g, 0.4 mol), 1,2-benzenedimethanol (69 g, 0.5 mol) and Dowex 50 acidic ion exchange resin (0.5 g) were added to a reaction flask, and the reaction temperature was set to 120° C. During the reaction process, the by-product methanol was continuously collected using a water separator, to evaluate the reaction progress according to the amount of the collected methanol. The reaction lasted for about 8 hours. After the reaction was completed, the acidic resin was removed by filtration. The obtained crude product was subjected to vacuum distillation to collect the fractions around 160° C. The product obtained above (43.77 g, 0.18 mol) was dissolved in 70 ml of dry tetrahydrofuran and placed in a reaction flask, then added with Aliquat 336 (1.67 g, 0.004 mol), as the reaction temperature was reduced to 0° C., gradually added with t-BuOK (40.41 g, 0.36 mol), and the temperature was maintained to react for 2 h. After the reaction was completed, the solid was removed by filtration, and the organic phase was concentrated to obtain a crude product, which was then distilled to collect the fraction around 96 to 99° C., namely the product BMDO.

0.1 mol cycloketene compound BMDO was mixed with benzoyl peroxide (BPO, 2 mol %) to obtain a component A; 0.1 mol co-monomer methacrylic acid (MA) and 0.03 mol % cross-linking agent bis(2-methacryloxyethyl)phosphate, $3 \times 10^{-6}$ mol % aminocaproic acid, $5 \times 10^{-7}$ mol % antibacterial peptide and N,N'-dimethyl-p-toluidine (DMPT, 2 mol %), were mixed evenly to form a component B for standby use. The component A and component B were quickly and uniformly mixed, and the obtained mixed solution was quickly and uniformly coated on the application site to undergo free radical ring-opening polymerization adhesion at room temperature.

Example 2.4

2-bromo-1,1'-dimethoxyethane (65 g, 0.4 mol), 1-phenyl-1,2-ethylene glycol (69 g, 0.5 mol) and Dowex 50 acidic ion exchange resin (0.5 g) were added into a reaction flask, in which the reaction temperature was set to 120° C. During the reaction process, the by-product methanol was continuously collected using a water separator, to evaluate the reaction progress according to the amount of the collected methanol. The reaction lasted for about 4 hours. After the reaction was completed, the acidic resin was removed by filtration. The obtained crude product was subjected to vacuum distillation to collect the fractions around 70° C. The product obtained above (43.77 g, 0.18 mol) was dissolved in 70 ml of dry tetrahydrofuran and placed in a reaction flask, then added with Aliquat 336 (1.67 g, 0.004 mol), as the reaction temperature was reduced to 0° C., gradually added with t-BuOK (40.41 g, 0.36 mol), and the temperature was maintained to react for 2 h. After the reaction was completed, the solid was removed by filtration, and the organic phase was concentrated to obtain a crude product, which was then distilled to collect the fraction around 50° C., namely the product MPDL.

0.1 mol cycloketene compound MPDL was mixed with benzoyl peroxide (BPO, 2 mol %) to obtain a component A; 0.01 mol co-monomer poly(ethylene glycol) methacrylate was mixed evenly, in which the mixed solution was slightly exothermic, then added with 0.01 mol % cross-linking agent bis(2-methacryloxyethyl)phosphate, $2 \times 10^{-6}$ mol % vitamin K1, $3 \times 10^{-7}$ mol % silver ions and N,N'-dimethyl-p-toluidine (DMPT, 2 mol %), and mixed evenly to form a component B for standby use. The component A and component B were quickly and uniformly mixed, and the obtained mixed solution was quickly and uniformly coated on the application site to undergo free radical ring-opening polymerization adhesion at room temperature.

Example 2.5

The preparation process of DMMDO was the same as that in Example 2.1.

0.1 mol cycloketene compound DMMDO was mixed with benzoyl peroxide (BPO, 2 mol %) to obtain a component A; 0.05 mol ethylene glycol vinyl ether (EGVE) and 0.05 mol % cross-linking agent bis(2-methacryloxyethyl)phosphate, $2 \times 10^{-6}$ mol % vitamin K4, $2 \times 10^{-7}$ mol % coumarin and N,N'-dimethyl-p-toluidine (DMPT, 2 mol %), were mixed evenly to form a component B for standby use. The component A and component B were quickly and uniformly mixed, and the obtained mixed solution was quickly and uniformly coated on the application site or in the polytetrafluoroethylene mold to undergo free radical ring-opening polymerization adhesion at room temperature.

Example 2.6

The preparation process of MDO was the same as that in Example 2.2.

0.1 mol cycloketene compound MDO was mixed with benzoyl peroxide (BPO, 2 mol %) to obtain a component A; 0.03 mol co-monomer 2-methacryloyloxyethyl phosphorylcholine (MPC) and 0.04 mol % cross-linking agent bis(2-methacryloxyethyl)phosphate, $3\times10^{-6}$ mol % sodium carboxysulfonate, $3\times10^{-7}$ mol % polyhexamethyleneguanidine hydrochloride and N,N'-dimethyl-p-toluidine (DMPT, 2 mol %), were mixed evenly to form a component B for standby use. The component A and component B were quickly and uniformly mixed, and the obtained mixed solution was quickly and uniformly coated on the application site to undergo free radical ring-opening polymerization adhesion at room temperature.

Comparative Example 2.1

A mixed solution of 10 g of 2-octyl cyanoacrylate (OCA) and 5 mg of p-toluenesulfonic acid (PTSA, stabilizer) was quickly and evenly coated on de-fat pork skin, which was covered with another piece of pork skin and slightly pressed for 20 s to realize adhesion by in-situ polymerization occurred at room temperature.

Comparative Example 2.2

A cycloketene compound DMMDO (10 g) and a co-monomer methacrylic acid (MA, 7.5 g) were mixed uniformly, in which the mixed solution was slightly exothermic, then added with 0.05 mol % cross-linking agent bis(2-methacryloxyethyl)phosphate, and mixed evenly for subsequent use; benzoyl peroxide (BPO, 2 mol %) was fully dissolved in the above-mentioned mixed solution, which was then added with N,N'-dimethyl-p-toluidine (DMPT, 2 mol %), and mixed quickly and uniformly. The mixed solution was quickly and uniformly coated on the application site to undergo free radical ring-opening polymerization adhesion at room temperature.

Test Experiment

In Vitro Adhesion Experiments

According to GB/T 7124-2008 standard, the in vitro bone tissue adhesion strength was obtained by shear adhesion test, and the shear adhesion model is shown in FIG. 3. Before the experiment, de-fat pork skin was selected and cut into regular plate-like splines, which had a length and width of 10 cm×2.5 cm, and a thickness of 0.2 cm, the preparation of which was as described in Examples 2.1 to 2.6 and Comparative example 2.1 to 2.2, wherein the adhesion area was 2.5 cm×1.0 cm. The obtained adhesive sample was placed at room temperature for 2 h and then subjected to a tensile test, which was carried out on a universal testing machine (LD-5 type of LLOYD company, sensor 2.5 kN), wherein the tensile rate was 5 mm/min. The shear adhesion strength was calculated by dividing the load force at the fracture of the adhesive sample by the adhesion area.

TABLE 2.1

| | In vitro adhesion strength (MPa) | | | |
|---|---|---|---|---|
| Experimental group | Comparative example 2.1 | Comparative example 2.2 | Example 2.1 | Example 2.2 |
| Adhesion strength | 1.6 ± 0.2 | 1.7 ± 0.3 | 1.7 ± 0.4 | 1.3 ± 0.2 |
| Experimental group | Example 2.3 | Example 2.4 | Example 2.5 | Example 2.6 |
| Adhesion strength | 1.5 ± 0.2 | 1.4 ± 0.3 | 1.2 ± 0.3 | 1.3 ± 0.4 |

It can be seen from Table 2.1 that the adhesion strengths of the materials in Examples 2.1 to 2.6 were all above 1 MPa, among which the maximum adhesion strength of Example 2.1 was greater than that of Comparative example 2.1, showing better adhesion performance; this is because, the preferred methacrylic acid can improve the polarity and hydrophilicity of the material, which can increase the contact and infiltration to the tissue, thereby improving the adhesion strength.

In Vitro Coagulation Assay

The whole blood used in the experiment was rabbit whole blood, containing sodium citrate anticoagulant with a mass fraction of 10%. The polymers prepared in Examples 2.1 to 2.6 and Comparative examples 2.1 to 2.2 were respectively placed in a polytetrafluoroethylene mold to be cured and molded, and then 0.1 g of each was weighed for use. 1 ml of fresh rabbit whole blood containing anticoagulant and 0.1 g of sample were put together in a centrifuge tube and incubated at 37° C. for 5 min, added with 100 μL of calcium chloride solution with a concentration of 0.025 mol/L and mixed well. The timer was started immediately, and the centrifuge tube was inverted every 5 s. When the blood stopped flowing, the timer was stopped, and the time for coagulation was recorded. The results are shown in Table 2.

TABLE 2.2

| | Statistical results data table of in vitro coagulation time (s) | | | | |
|---|---|---|---|---|---|
| Experimental group | Negative control | Comparative example 2.1 | Comparative example 2.2 | Example 2.1 | Example 2.2 |
| Coagulation time | 600 ± 10 | 400 ± 15 | 410 ± 10 | 35 ± 5 | 30 ± 10 |
| Experimental group | | Example 2.3 | Example 2.4 | Example 2.5 | Example 2.6 |
| Coagulation time | | 40 ± 5 | 35 ± 15 | 40 ± 5 | 45 ± 5 |

The results of in vitro coagulation time are shown in Table 2.2, in which the negative control group was blood only added with 100 μL of calcium chloride with a concentration of 0.025 mol/L. Compared with Comparative example 2.1 and Comparative example 2.2, the coagulation time in Examples 2.1 to 2.6 was significantly decreased, this is because hemostatic agents, such as halloysite, haemocoagulase, aminocaproic acid and vitamin K1 were added in Examples 2.1 to 2.6. These hemostatic agents can better promote blood coagulation after contacting with blood, significantly reducing the in vitro coagulation time, and enabling the adhesive to exert a rapid hemostatic function while sealing the wound.

In Vitro Antibacterial Experiment

The polymers prepared in Examples 2.1 to 2.6 and Comparative examples 2.1 to 2.2 were respectively placed in a polytetrafluoroethylene mold to be cured and molded, then cut into 1.5 cm×1.5 cm square samples for later use. According to the requirements of the GB/T 31402 standard for the evaluation of antibacterial property, *Staphylococcus aureus* and *Escherichia coli* were selected to be the test strains. The square samples prepared in Examples 2.1 to 2.6 and Comparative examples 2.1 to 2.2 were subjected to the antibacterial property test by strictly following the experimental procedures described in the GB/T 31402 standard.

TABLE 2.3

| Bactericidal rate of *Staphylococcus aureus* and *Escherichia coli* (%) | | | | |
| --- | --- | --- | --- | --- |
| Experimental group | Comparative example 2.1 | Comparative example 2.2 | Example 2.1 | Example 2.2 |
| Bactericidal rate of *S. aureus* | 5.2 ± 0.2 | 6.1 ± 0.5 | 98.3 | 97.2 |
| Bactericidal rate of *E. coli* | 2.3 ± 0.3 | 4.2 ± 0.2 | 96.4 | 95.5 |
| Experimental group | Example 2.3 | Example 2.4 | Example 2.5 | Example 2.6 |
| Bactericidal rate of *S. aureus* | 96.2 | 99.8 | 98.5 | 97.6 |
| Bactericidal rate of *E. coli* | 97.1 | 99.6 | 96.5 | 96.2 |

The results of the in vitro antibacterial experiments are shown in Table 2.3. After added with the antibacterial agents such as benzalkonium bromide, polyhexamethylene guanidine, antibacterial peptides and silver ions, Examples 2.1 to 2.6 had a bactericidal rate reaching more than 95% to both the *Staphylococcus aureus* and *Escherichia coli*, indicating that the adhesives prepared in Examples 2.1 to 2.6 had obvious bactericidal effect on both Gram-negative bacteria and Gram-positive bacteria.

Rat Liver Hemostasis Experiment

In the present disclosure, the in vivo hemostatic function detection on the polymers obtained in Examples 2.1 to 2.6 and Comparative examples 2.1 to 2.2 was performed, and the specific detection method is as follows:

The liver hemorrhage of SD rat was taken as a model, the rat was anesthetized with 5% isoflurane, maintained with 1.5% isoflurane, and shaved off the abdominal hair. The abdominal cavity of the rat was opened along the linea alba to find and expose the liver of the rat, a 0.5 cm wound was created on the left hepatic lobe of the rat with a scalpel, and the samples mixed in an equal volume was dripped on the surface of the liver wound to observe the hemostasis state and record the hemostasis time.

TABLE 2.4

| Hemostasis time (s) of rat liver hemorrhage model | | | | | |
| --- | --- | --- | --- | --- | --- |
| Experimental group | Blank control | Comparative example 2.1 | Comparative example 2.2 | Example 2.1 | Example 2.2 |
| Hemostasis time | 350 ± 20 | 220 ± 15 | 160 ± 10 | 40 ± 5 | 35 ± 5 |
| Experimental group | Example 2.3 | Example 2.4 | Example 2.5 | Example 2.6 | |
| Hemostasis time | 45 ± 5 | 40 ± 10 | 45 ± 10 | 50 ± 5 | |

The results of hemostasis time of the rat liver hemorrhage model are shown in Table 2.4, wherein the blank control group was an untreated rat liver hemorrhage model. In Comparative example 2.1 and Comparative example 2.2, the hemorrhage of the rat liver was relieved after curing, which may be caused by the sealing effect of the cured adhesive on the wound. More preferably, the time used for hemostasis of rat liver in Examples 2.1 to 2.6 was significantly lower than that in Comparative examples 2.1 to 2.2, which may be due to the fact that on the basis of sealing wounds, Examples 2.1 to 2.6 were added with hemostatic agents such as halloysite, haemocoagulase, aminocaproic acid and vitamin K1, which can activate the coagulation cascade reaction after contacting with blood, and promote blood coagulation faster, thereby enabling the adhesives prepared in Examples 2.1 to 2.6 to exert a rapid hemostatic function while sealing the wound.

As can be seen from the above examples, the present disclosure provides an absorbable rapid hemostatic adhesive, comprising a component A and a component B: the component A comprises a cycloketene acetal compound and an oxidizing agent; the component B comprises a vinyl monomer, a cross-linking agent, a hemostatic agent and a reducing agent. The adhesive provided by the present disclosure is formed by in-situ curing of free radical ring-opening polymerization under the initiation of a redox free radical polymerization initiator in the human body environment, during which the adhesion is fast, and the reaction is slightly exothermic, which will not burn the human body. After the free radical ring-opening polymerization of cycloketene acetal compound, the main chain contains a structure of ester bond, which can be degraded in a physiological environment with an 8-week degradation rate of more than 20%. The mild reaction conditions are conducive to the loading of the hemostatic agent and antibacterial agent. The gradual exposure and release of these substances further impart activated hemostatic efficacy to the adhesive and avoid bacterial infection. The adhesive is ready-to-use, and has a simple use process, an ideal implementation time window of 1 to 5 min, and strong clinical maneuverability.

Example 3.1

The preparation process of cycloketene compound DMMDO:
2,5-hexanediol (1.2 g, 10.2 mmol) was dissolved in a solution of dichloromethane (170 ml) and pyridine (7.5 ml, 91.5 mmol), the reaction system was replaced with argon at −20° C., then dropwise added with a solution of triphosgene (4.55 g, 15.2 mmol) in dichloromethane (90 ml) to react at room temperature for 20 min. Then the product mixed solution quenched with saturated ammonium chloride (100 ml) was extracted with dichloromethane to obtain the organic phase, which was washed with saturated brine, dried over anhydrous sodium sulfate, filtered, sucking filtered in vacuum, distilled under reduced pressure to collect the fractions around 95° C. The product of the above system (0.023 g, 0.16 mmol) was dissolved in tetrahydrofuran/toluene (1:1) mixed solvent, and added with Petasis reagent (2 ml, 0.5 mmol, 5 a tetrahydrofuran/toluene mixed solution with a concentration of 5 wt %), mixed well and replaced with argon to react in the dark at 60 to 65° C. for 20 h. The product was precipitated with 10 ml n-hexane, filtered, and concentrated to obtain DMMDO.

The cycloketene compound DMMDO (0.1 mol) was mixed with benzoyl peroxide (BPO, 2 mol %) to obtain a component A; a co-monomer methacrylic acid (NIA, 2 mol %) and 1 mol % cross-linking agent bis(2-methacryloxyethyl)phosphate, $1\times10^{-6}$ mol % vancomycin, $2\times10^{-7}$ mol % dextran and N,N'-dimethyl-p-toluidine (DMPT, 2 mol %) were mixed evenly to form a component B for standby use. The component A and component B were quickly and uniformly mixed, and the obtained mixed solution was quickly and uniformly coated on de-fat pork skin, which was covered with another piece of pork skin, and slightly pressed for more than 20 s to undergo free radical ring-opening polymerization adhesion at room temperature.

Example 3.2

The preparation process of cycloketene compound MDO:
2-bromo-1,1'-dimethoxyethane (65 g, 0.4 mol), 1,4-butanediol (36 g, 0.51 mol) and Dowex 50 acidic ion exchange resin (0.5 g) were added to a reaction flask to react at 115° C. for about 4 h (the progress of the reaction was evaluated according to the amount of by-product methanol collected). The reaction solution was filtered to remove the acidic resin, and distilled under reduced pressure to collect the fractions around 95° C. The above product (35 g, 0.18 mol) was dissolved in 70 ml of anhydrous tetrahydrofuran, then added with Aliquat 336 (1.67 g, 0.004 mol) into the above mentioned reaction flask, as the reaction temperature was reduced to 0° C., gradually added with t-BuOK (40.41 g, 0.36 mol), and the temperature was maintained to react for 2 h. The solid was removed by filtration, and the organic phase was concentrated and distilled to collect the fraction around 25° C., namely MDO.

The cycloketene compound MDO (0.1 mol) was mixed with benzoyl peroxide (BPO, 2 mol %) to obtain a component A; a co-monomer 10-(phosphonooxy)decyl methacrylate (MDP, 2 mol %) and 2 mol % cross-linking agent bis(2-methacryloxyethyl)phosphate, $2\times10^{-6}$ mol % azithromycin, $3\times10^{-7}$ mol % hyaluronic acid and N,N'-dimethyl-p-toluidine (DMPT, 2 mol %) were mixed evenly to form a component B for standby use. The component A and component B were quickly and uniformly mixed, and the obtained mixed solution was quickly and uniformly coated on de-fat pork skin, which was covered with another piece of pork skin, and slightly pressed for more than 20 s to undergo free radical ring-opening polymerization adhesion at room temperature.

Example 3.3

The preparation process of cycloketene compound BMDO:
2-bromo-1,1'-dimethoxyethane (65 g, 0.4 mol), 1,2-benzenedimethanol (69 g, 0.5 mol) and Dowex 50 acidic ion exchange resin (0.5 g) were added to a reaction flask to react at 120° C. reaction for about 8 h (the progress of the reaction was evaluated according to the amount of by-product methanol collected). The reaction solution was filtered to remove the acidic resin, and distilled under reduced pressure to collect the fractions around 160° C. The above product (43.77 g, 0.18 mol) was dissolved in 70 ml of anhydrous tetrahydrofuran, then added with Aliquat 336 (1.67 g, 0.004 mol) into the above mentioned reaction flask, as the reaction temperature was reduced to 0° C., gradually added with t-BuOK (40.41 g, 0.36 mol), and the temperature was maintained to react for 2 h. The solid was removed by filtration, and the organic phase was concentrated and distilled to collect the fraction around 96 to 99° C., namely BMDO The cycloketene compound BMDO (0.1 mol) was mixed with benzoyl peroxide (BPO, 2 mol %) to obtain a component A; a co-monomer methacrylic acid (MA, 2 mol %) and 3 mol % cross-linking agent bis(2-methacryloxyethyl)phosphate, $3\times10^{-6}$ mol % antibacterial peptide, $4\times10^{7}$ mol % asiaticoside and N,N'-dimethyl-p-toluidine (DMPT, 2 mol %) were mixed evenly to form a component B for standby use. The component A and component B were quickly and uniformly mixed, and the obtained mixed solution was quickly and uniformly coated on de-fat pork skin, which was covered with another piece of pork skin, and slightly pressed for more than 20 s to undergo free radical ring-opening polymerization adhesion at room temperature.

Example 3.4

The preparation process of cycloketene compound MPDL:
2-bromo-1,1'-dimethoxyethane (65 g, 0.4 mol), 1-phenyl-1,2-ethylene glycol (69 g, 0.5 mol) and Dowex 50 acidic ion exchange resin (0.5 g) were added into a reaction flask to react at 120° C. for about 4 h (the progress of the reaction was evaluated according to the amount of by-product methanol collected). The reaction solution was filtered to remove the acidic resin, and distilled under reduced pressure to collect the fractions around 70° C. The above product (43.77 g, 0.18 mol) was dissolved in 70 ml of anhydrous tetrahydrofuran, then added with Aliquat 336 (1.67 g, 0.004 mol) into the above mentioned reaction flask, as the reaction temperature was reduced to 0° C., gradually added with t-BuOK (40.41 g, 0.36 mol), and the temperature was maintained to react for 2 h. The solid was removed by filtration, and the organic phase was concentrated and distilled to collect the fraction around 50° C., namely MPDL.

The cycloketene compound MPDL (0.1 mol) was mixed with benzoyl peroxide (BPO, 2 mol %) to obtain a component A; a co-monomer 10-(phosphonooxy)decyl methacrylate (MDP, 2 mol %), 3 mol % cross-linking agent bis(2-methacryloxyethyl)phosphate, $2\times10^{-6}$ mol % benzalkonium chloride, $5\times10^{-7}$ mol % hyaluronic acid and N,N'-dimethyl-p-toluidine (DMPT, 2 mol %) were mixed evenly to form a component B for standby use. The component A and component B were quickly and uniformly mixed, and the obtained mixed solution was quickly and uniformly coated on de-fat pork skin, which was covered with another piece of pork skin, and slightly pressed for more than 20 s to undergo free radical ring-opening polymerization adhesion at room temperature.

Example 3.5

The preparation process of the cycloketene compound BMDO was the same as that in Example 3.3.

The cycloketene compound BMDO (0.1 mol) was mixed with benzoyl peroxide (BPO, 2 mol %) to obtain a component A; a co-monomer sulfobetaine methacrylate (SBMA, 2 mol %), 3 mol % cross-linking agent bis(2-methacryloxyethyl)phosphate, 7×10−6 mol % coumarin, $4\times10^{7}$ mol % asiaticoside and N,N'-dimethyl-p-toluidine (DMPT, 2 mol %), were mixed evenly to form a component B for standby use. The component A and component B were quickly and uniformly mixed, and the obtained mixed solution was quickly and uniformly coated on de-fat pork skin, which was covered with another piece of pork skin, and slightly pressed for more than 20 s to undergo free radical ring-opening polymerization adhesion at room temperature.

Example 3.6

The preparation process of the cycloketene compound MPDL was the same as that in Example 3.4.

The cycloketene compound MPDL (0.1 mol) was mixed with benzoyl peroxide (BPO, 2 mol %) to obtain a component A; a co-monomer dopamine methacrylamide (DMA, 2 mol %), 3 mol % cross-linking agent bis(2-methacryloxyethyl)phosphate, $2\times10^{-6}$ mol % zinc ions, $5\times10^{-7}$ mol % hyaluronic acid and N,N'-dimethyl-p-toluidine (DMPT, 2 mol %), were mixed evenly to form a component B for standby use. The component A and component B were quickly and uniformly mixed, and the obtained mixed solution was quickly and uniformly coated on de-fat pork skin, which was covered with another piece of pork skin, and slightly pressed for more than 20 s to undergo free radical ring-opening polymerization adhesion at room temperature.

Comparative Example 3.1

A mixed solution of 10 g of 2-octyl cyanoacrylate (OCA) and 5 mg of p-toluenesulfonic acid (PTSA, stabilizer) was coated on de-fat pork skin, which was covered with another piece of pork skin, and pressed slightly for more than 20 s to realize adhesion by in-situ polymerization occurred at room temperature.

In Vitro Adhesion Experiment

According to GB/T 7124-2008 standard, the in vitro adhesion strength was obtained by shear adhesion test, and the shear adhesion model is shown in FIG. 3. Before the experiment, de-fat pork skin was selected and cut into regular plate-like splines, which had a length and width of 10 cm×2.5 cm, and a thickness of 0.2 cm, the preparation of which was as described in Examples 3.1 to 3.6 and Comparative example 3.1, wherein the adhesion area was 2.5 cm×1.0 cm; the obtained adhesive sample was placed at room temperature for 2 h and then subjected to a tensile test, which was carried out on a universal testing machine (LD-5 type of LLOYD company, sensor 2.5 kN), wherein the tensile rate was 5 mm/min. The shear adhesion strength was calculated by dividing the load force at the fracture of the adhesive sample by the adhesion area.

TABLE 3.1

| | In vitro adhesion strength (KPa) | | | | | | |
|---|---|---|---|---|---|---|---|
| Cycloketene:co-monomer (mol:mol) | Comparative example 3.1 | Example 3.1 | Example 3.2 | Example 3.3 | Example 3.4 | Example 3.5 | Example 3.6 |
| 2:1 | 40.1 ± 0.7 | 165.8 ± 0.1 | 175.2 ± 0.3 | 160.5 ± 0.2 | 180.4 ± 0.1 | 162.8 ± 0.1 | 200.3 ± 0.2 |
| 1:1 | | 175.4 ± 0.3 | 182.8 ± 0.2 | 170.9 ± 0.1 | 187.8 ± 0.2 | 171.7 ± 0.2 | 207.5 ± 0.3 |
| 1:2 | | 180.6 ± 0.2 | 190.2 ± 0.1 | 178.3 ± 0.2 | 192.9 ± 0.1 | 180.3 ± 0.2 | 215.9 ± 0.1 |

The adhesion test results are shown in Table 3.1.

As shown in Table 3.1: the adhesion strength of the materials in Examples 3.1-3.6 was all above 160 KPa, among which the maximum adhesion strength was higher than that of Comparative example 3.1, showing good adhesion performance. It can be seen that with the increase of the proportion of co-monomers, the adhesion strength of the materials gradually increased, this is because the preferred co-monomer 10-(phosphonooxy)decyl methacrylate and dopamine methacrylamide can improve the polarity and hydrophilicity of the material, improving the contact and infiltration to the tissue, and the phosphate group and dopamine group in their structure can achieve covalent binding with tissue, so it has high adhesion strength. In addition, the preferred active ingredients dextran, hyaluronic acid and asiaticoside in the copolymer had an effect of molecular chain reinforcement, improving the mechanical strength of the material, and the hydroxyl group on the molecular chain thereof can form a hydrogen bond interaction with the amino group on the tissue, thereby further improving the adhesion strength In Vitro Cytocompatibility Assay According to the requirements of the cytotoxicity test in GB/T16886 "Biological Evaluation of Medical Devices", MC3T3E1 was selected as the test cell line, and the cured samples in Examples 3.1 to 3.6 were prepared and shaped into a sample size of 0.5 cm×0.5 cm. After sterilized, the samples were placed in the culture medium to prepare the sample extract, 5 extract samples were prepared in each group. The sample medium extract was used to culture L929 cell under a condition of 37° C. and 5% $CO_2$ for 24 h. The cell viability was detected by CCK8 method, and the average of results of each group was taken.

Figure 9:
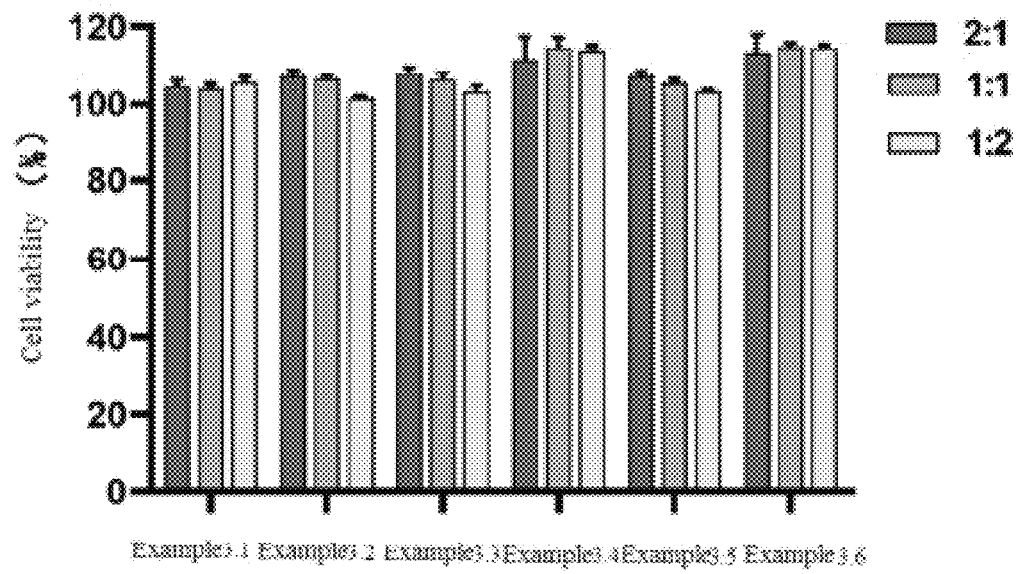
FIG. 9 is the cytocompatibility test diagram of the materials prepared in Examples 3.1 to 3.6 of the present disclosure.

The cytocompatibility test of the materials in Examples 3.1 to 3.6 is shown in FIG. 9.

As shown in FIG. 9, the materials in Examples 3.1 to 3.6 all showed good cell compatibility, which could significantly promote cell growth, and the cell viability was all above 100%.

In Vivo Degradation Assay

Balb/c mice (20 g, female) were shaved off back hairs in a sterile environment, whose skins were cleaned, then placed in an isoflurane-containing anesthesia box for anesthesia, fixed on an operating table, and maintained under anesthesia with a breathing mask. The dorsal skin of mice was sterilized with iodophor, and cut out an opening ((about 1 cm) with a scalpel, and the fascia between the skin and muscle was separated with scissors and forceps to form a small pocket. The cured samples in Comparative examples 3.1 and Examples 3.1 to 3.6 were made into a size of 0.5 cm×0.5 cm, and implanted under the dorsal skin of mice. The tissue was sutured, and disinfected with iodophor again. 6 mice were randomly implanted in each case. After fed for 8 weeks, the mice were euthanized. The samples of Comparative examples 3.1 and Examples 3.1 to 3.6 were taken out to observe the morphology of the samples, and to weigh the weight of the samples. The degradation rate was calculated by comparing with the samples before implanted.

Figure 10:
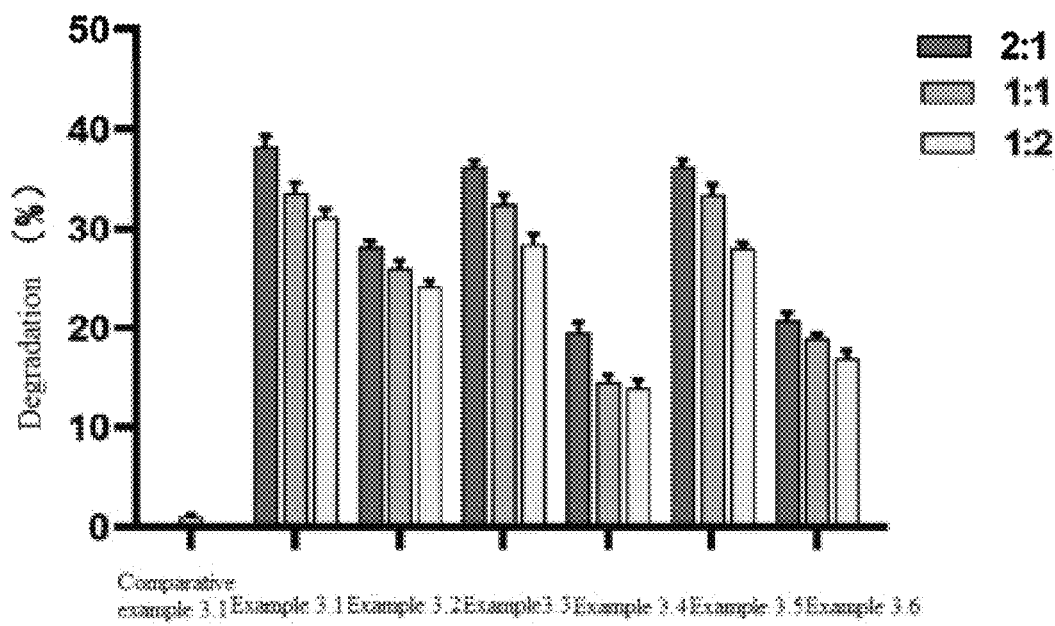
FIG. 10 is the in vivo degradation test diagram of the materials in Comparative example 3.1 and Examples 3.1 to 3.6 of the present disclosure.

The in vivo degradation test of the materials in Comparative example 3.1 and Examples 3.1 to 3.6 is shown in FIG. 10.

As shown in FIG. 10: the materials in Examples 3.1 to 3.6 all showed good degradation rates after being maintained in a physiological environment for 8 weeks. The degradation of the materials in Examples 3.1, 3.2, 3.3 and 3.5 was the most obvious, wherein the maximum degradation rate could reach 38.5%; and with the increase of the proportion of DMMDO/BMDO, the degradation degree of the material was more obvious, indicating that the introduction of MDO ring-opening polymer and the ester bond on the side chain thereof provided good degradability for the material. In addition, the degradation rate of the material in Comparative example 3.1 for 8 weeks was 1.1%, which showed that the degradability of the material was poor, much lower than that in Examples 3.1 to 3.6, indicating that the tissue adhesive material constructed by the present disclosure had excellent degradability in vivo.

It can be seen from the above examples that compared with the prior art, the absorbable medical soft tissue adhesive provided by the present disclosure is formed by in-situ curing of free radical ring-opening polymerization under the initiation of a redox free radical polymerization initiator in the human body environment. The reaction process is rapid with a curing time of 20 s to 3 min, and the reaction is slightly exothermic, which will not burn the human body. After the free radical ring-opening polymerization of cycloketene acetal compound, the main chain contains a structure of ester bond, which can be degraded in a physiological environment (8 week degradation rate>20%), and has good degradability. The mild reaction conditions are conducive to the loading of antibacterial agents and substances that promote tissue and organ healing. With the degradation of the adhesive, these substances are gradually exposed and released to promote tissue healing and avoid bacterial infection. The adhesive quickly obtains high mechanical strength and adhesion strength, wherein the adhesion strength within 5 min is >160 KPa, which is not easy to be swollen under physiological environment, and has good physiological stability.

Example 4.1

The preparation process of cycloketene acetal compound MDO:

2-bromo-1,1'-dimethoxyethane (65 g, 0.4 mol), 1,4-butanediol (36 g, 0.51 mol) and Dowex 50 acidic ion exchange resin (0.5 g) were added to a reaction flask, in which the reaction temperature was set to 115° C. During the reaction process, the by-product methanol was continuously collected using a water separator, to evaluate the reaction progress according to the amount of the collected methanol. The reaction lasted for about 4 hours. After the reaction was completed, the acidic resin was removed by filtration. The obtained crude product was subjected to vacuum distillation to collect the fractions at 95° C. The product obtained above (35 g, 0.18 mol) was dissolved in 70 ml of dry tetrahydrofuran and placed in a reaction flask, then added with Aliquat 336 (1.67 g, 0.004 mol), as the reaction temperature was reduced to 0° C., gradually added with t-BuOK (40.41 g, 0.36 mol), and the temperature was maintained to react for 2 h. After the reaction was completed, the solid was removed by filtration, and the organic phase was concentrated to obtain a crude product, which was then distilled to collect the fraction at 25° C., namely the product MDO.

The cycloketene acetal compound MDO (11.4 g, 0.1 mol) and benzoyl peroxide (BPO, 0.48 g, 0.002 mol) were mixed uniformly to obtain a mixed solution A; a vinyl monomer 3-(methacryloyloxy)propyltrimethoxysilane (24.8 g, 0.1 mol), 2 mol % cross-linking agent poly(ethylene glycol) dimethacrylate and bioactive glass (particle size of 45 μm, 5 wt %) supported N,N'-dimethyl-p-toluidine (DMPT, 1 mol %) were uniformly mixed to obtain a mixed solution B. The mixed solution A and mixed solution B were rapidly mixed, and in-situ cured to obtain an absorbable bioactive bone cement; the bone cement was drawn with a syringe and injected to the desired site at dough phase with the aid of imaging.

Example 4.2

The preparation process of cycloketene acetal compound MPDL:

2-bromo-1,1'-dimethoxyethane (65 g, 0.4 mol), 1-phenyl-1,2-ethylene glycol (69 g, 0.5 mol) and Dowex 50 acidic ion exchange resin (0.5 g) were added into a reaction flask, in which the reaction temperature was set to 120° C. During the reaction process, the by-product methanol was continuously collected using a water separator, to evaluate the reaction progress according to the amount of the collected methanol. The reaction lasted for about 4 hours. After the reaction was completed, the acidic resin was removed by filtration. The obtained crude product was subjected to vacuum distillation to collect the fractions around 70° C. The product obtained above (43.77 g, 0.18 mol) was dissolved in 70 ml of dry tetrahydrofuran and placed in a reaction flask, then added with Aliquat 336 (1.67 g, 0.004 mol), as the reaction temperature was reduced to 0° C., gradually added with t-BuOK (40.41 g, 0.36 mol), and the temperature was maintained to react for 2 h. After the reaction was completed, the solid was removed by filtration, and the organic phase was concentrated to obtain a crude product, which was then distilled to collect the fraction around 50° C., namely the product MPDL.

The cycloketene acetal compound MPDL (16.2 g, 0.1 mol) and benzoyl peroxide (BPO, 0.48 g, 0.002 mol) were mixed uniformly to obtain a mixed solution A; a vinyl monomer methyl methacrylate (10 g, 0.1 mol), 2 mol % cross-linking agent poly(ethylene glycol) dimethacrylate and β-tricalcium phosphate (30 m, 5 wt %) supported N,N'-dimethyl-p-toluidine (DMPT, 1 mol %) were uniformly mixed to obtain a mixed solution B. The mixed solution A and mixed solution B were rapidly mixed, and in-situ cured to obtain an absorbable bioactive bone cement; the bone cement was drawn with a syringe and injected to the desired site at dough phase with the aid of imaging.

Example 4.3

The preparation process of cycloketene acetal compound BMDO:

2-bromo-1,1'-dimethoxyethane (65 g, 0.4 mol), 1,2-benzenedimethanol (69 g, 0.5 mol) and Dowex 50 acidic ion exchange resin (0.5 g) were added to a reaction flask, in which the reaction temperature was set to 120° C. During the reaction process, the by-product methanol was continuously collected using a water separator, to evaluate the reaction progress according to the amount of the collected methanol. The reaction lasted for about 8 hours. After the reaction was completed, the acidic resin was removed by filtration. The obtained crude product was subjected to vacuum distillation to collect the fractions at 160° C. The product obtained above (43.77 g, 0.18 mol) was dissolved in 70 ml of dry tetrahydrofuran and placed in a reaction flask, then added with Aliquat 336 (1.67 g, 0.004 mol), as the reaction temperature was reduced to 0° C., gradually added with t-BuOK (40.41 g, 0.36 mol), and the temperature was maintained to react for 2 h. After the reaction was completed, the solid was removed by filtration, and the organic phase was concentrated to obtain a crude product, which was then distilled to collect the fraction around 96 to 99° C., namely the product BMDO.

The cycloketene acetal compound BMDO (16.2 g, 0.1 mol) and benzoyl peroxide (BPO, 0.48 g, 0.002 mol) were mixed uniformly to obtain a mixed solution A; a vinyl monomer N-tert-butylacrylamide (12.7 g, 0.1 mol), 2 mol % cross-linking agent poly(ethylene glycol) dimethacrylate and nano-hydroxyapatite (80 m, 5 wt %) supported N,N'-dimethyl-p-toluidine (DMPT, 1 mol %) were uniformly mixed to obtain a mixed solution B. The mixed solution A and mixed solution B were quickly mixed, and in-situ cured to obtain an absorbable bioactive bone cement; the bone cement was drawn with a syringe and injected to the desired site at dough phase with the aid of imaging.

Example 4.4

The preparation process of cycloketene acetal compound DMMDO:

2,5-hexanediol (1.2 g, 10.2 mmol) was dissolved in dichloromethane (170 ml) and pyridine (7.5 ml, 91.5 mmol). The reaction system was placed at −20° C. and replaced with argon, and then added dropwise with a solution of triphosgene (4.55 g, 15.2 mmol) in dichloromethane (90 ml). After the addition was completed, the mixture was returned to room temperature to react for 20 min. Then the reaction was quenched using a saturated ammonium chloride solution (100 ml), the product mixed solution was extracted with dichloromethane to obtained the organic phase, which was washed with saturated brine, dried over anhydrous sodium sulfate, filtered, removed off solvent in vacuum, and distilled under reduced pressure to collect the fraction around 95° C. The product obtained above (0.023 g, 0.16 mmol) was dissolved in tetrahydrofuran/toluene (1:1) mixed solvent, and added with Petasis reagent (2 ml, 0.5 mmol, a tetrahydrofuran/toluene mixed solution with a concentration of 5 wt %), the reaction system was replaced with argon to react at 60 to 65° C. in the dark for 20 h. After the reaction was completed, n-hexane (10 ml) was added to form a yellow precipitate. After filtration, the filtrate was concentrated to obtain a product DMMDO.

The cycloketene acetal compound DMMDO (14.2 g, 0.1 mol) and benzoyl peroxide (BPO, 0.48 g, 0.002 mol) were mixed uniformly to obtain a mixed solution A; vinyl acetate (8.6 g, 0.1 mol) was mixed well, then added with 2 mol % cross-linking agent poly(ethylene glycol) dimethacrylate and bioactive glass (45 μm, 5 wt %) supported N,N'-dimethyl-p-toluidine (DMPT, 1 mol %), and the mixture was uniformly mixed to obtain a mixed solution B. The mixed solution A and the mixed solution B were rapidly mixed, and in-situ cured to obtain an absorbable bioactive bone cement; the bone cement was drawn with a syringe and injected to the desired site at dough phase with the aid of imaging.

Comparative Example 4.1

The solid phase and the liquid phase of the commercially available bone cement OSTEOPAL® were mixed uniformly according to the instructions for use, and then the bone cement was drawn with a syringe and injected to the desired site at dough phase with the aid of imaging.

The Maximum Curing Temperature and Curing Time

The solid and liquid phases of the bone cement materials of the Examples and Comparative examples were mixed uniformly and injected into the prefabricated mold immediately, and the timer was started. The temperature was continuously measured and observed in real time by means of a thermocouple. The test was terminated when the temperature began to decrease. According to the obtained curve of temperature versus time, the peak value was read as the maximum curing temperature. At the same time, the curing time of bone cement was defined to be the time corresponding to the average curing temperature (the average of the maximum curing temperature and room temperature) on the curve. The maximum curing temperature and curing time of the materials in Comparative example 4.1 and Examples 4.1 to 4.4 are shown in Table 4.1.

TABLE 4.1

The maximum curing temperature and curing time of the bone cement materials of the Examples and Comparative examples.

| Sample | The maximum curing temperature | Curing time |
| --- | --- | --- |
| Comparative example 4.1 | 64.7° C. | 17.5 min |
| Example 4.1 | 37.2° C. | 15.7 min |
| Example 4.2 | 32.4° C. | 19.6 min |
| Example 4.3 | 41.6° C. | 13.8 min |
| Example 4.4 | 36.3° C. | 17.4 min |

The results show that the curing temperature of the absorbable bioactive bone cement of the present disclosure was significantly lower than that of the traditional PMMA bone cement. In the shown examples, not much heat was generated during the curing, and the maximum curing temperature was not higher than 42° C. Especially in Example 4.1, the maximum temperature was 37.2° C., which is very close to the normal temperature of the human body, and the shortened curing time window can also meet the clinical operation requirements.

Mechanical Properties Test of Bone Cement

The mechanical properties of bone cement were tested according to IS05833-2002. The solid phase and liquid phase of the bone cement materials of the Examples and Comparative examples were contacted, mixed uniformly, immediately injected into a cylindrical mold with a diameter of 5 mm and a height of 10 mm, and demolded after cured. The prepared samples were subjected to compression test on a universal testing machine (LD-5 type of LLOYD company, sensor 2.5 kN). The loading speed was 5 mm/min, and the test was stopped when the compression rate was 30%. The compressive strength value and the elastic modulus of the bone cement were calculated according to the stress-strain curve. There were 5 parallel samples in each group, and the average value of the results was taken. In addition, a rectangular sample strip was prepared to measure the flexural strength of bone cement by three-point bending test method, wherein the loading speed was 5 mm/min, the loading was continued until the sample strip broke and the test was stopped. There were 5 parallel samples in each group, and the average value of the results was taken. The compressive strength, elastic modulus and flexural strength of the bone cement are shown in Table 4.2.

TABLE 4.2

Mechanical properties of the bone cement materials of the examples and comparative examples.

| Sample | Compressive strength (MPa) | Elastic modulus (GPa) | Flexural strength (MPa) |
|---|---|---|---|
| Comparative example 4.1 | 87 | 3.1 | 58 |
| Example 4.1 | 95.2 | 2.7 | 67 |
| Example 4.2 | 83.6 | 2.3 | 62 |
| Example 4.3 | 98.5 | 3.1 | 73 |
| Example 4.4 | 89.4 | 2.2 | 59 |

The results show that compared with the commercial bone cement products, the absorbable bioactive bone cement of the present disclosure had improved compressive strength and flexural strength, and had higher toughness.

In Vivo Degradation Assay

Balb/c mice (20 g, female) were shaved off back hairs in a sterile environment, whose skins were cleaned, then placed in an isoflurane-containing anesthesia box for anesthesia, fixed on an operating table, and maintained under anesthesia with a breathing mask. The dorsal skin of mice was sterilized with iodophor, and cut out an opening (about 1 cm) with a scalpel, and the fascia between the skin and muscle was separated with scissors and forceps to form a small pocket. The cured samples in Comparative example 4.1 and Examples 4.1 to 4.4 were made into a disk with a diameter of 5 mm and a height of 2 mm, and implanted under the dorsal skin of mice. The tissue was sutured, and disinfected with iodophor again. 6 mice were randomly implanted in each case. After fed for 8 weeks, the mice were euthanized. The samples of Comparative example 4.1 and Examples 4.1 to 4.4 were taken out to observe the morphology of the samples, and to weigh the weight of the samples. The degradation rate was calculated by comparing with the samples before implanted.

Figure 11:
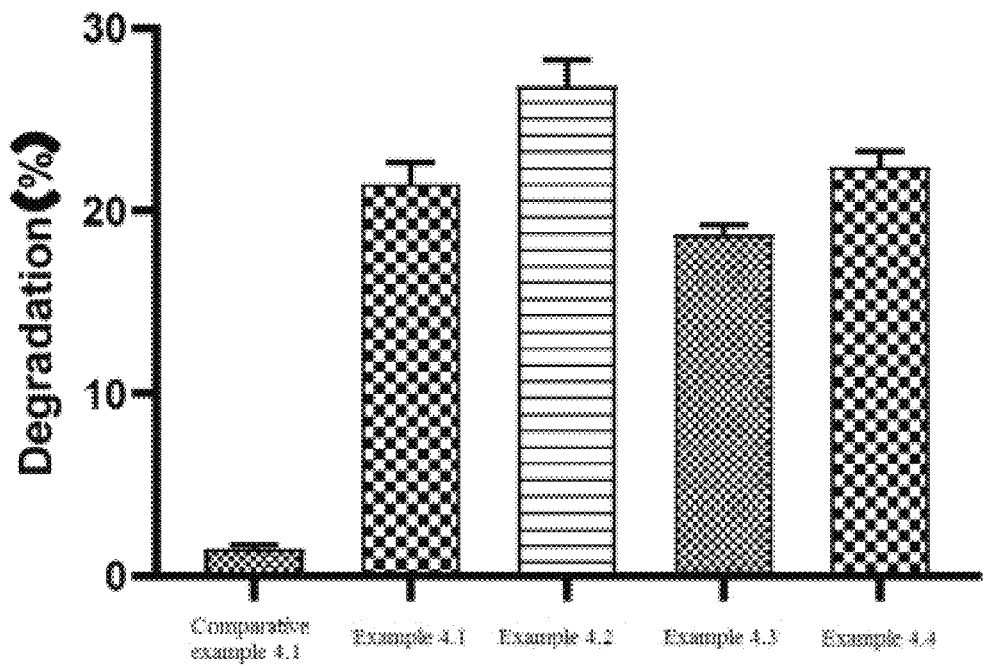
FIG. 11 is the in vivo degradation test diagram of the materials in Comparative example 4.1 and Examples 4.1 to 4.4 of the present disclosure.

The in vivo degradation test of the materials in Comparative example 4.1 and Examples 4.1 to 4.4 is shown in FIG. 11.

As shown in FIG. 11: the materials in Examples 4.1 to 4.4 all showed good degradation rates after being maintained in a physiological environment for 8 weeks. The material in Example 4.2 had the most obvious degradation, wherein the degradation rate could reach 26.86%; indicating that the introduction of MDO ring-opening polymerization provided good degradability for the material. In addition, the degradation rate of the material in Comparative example 4.1 for 8 weeks was 1.49%, suggesting the degradation of the material was poor, far lower than that of Examples 4.1 to 4.4, indicating that the bone cement constructed by the present disclosure had excellent degradability in vivo.

Osteogenic Activity Assay

ALP activity detection: After the osteoblast MC3T3E1 was cultured in the prefabricated samples of Examples 4.1 to 4.4 and Comparative example 4.1 for 7 days and 14 days, respectively, the old medium was removed, and the cells were washed with PBS for 1 to 3 times, and then added with RIAP cell lysate. After the cells were fully lysed, the cell lysate was centrifuged to take the supernatant, and the ALP activity of the cells was detected according to the instructions of the AKP/ALP kit.

Figure 12:
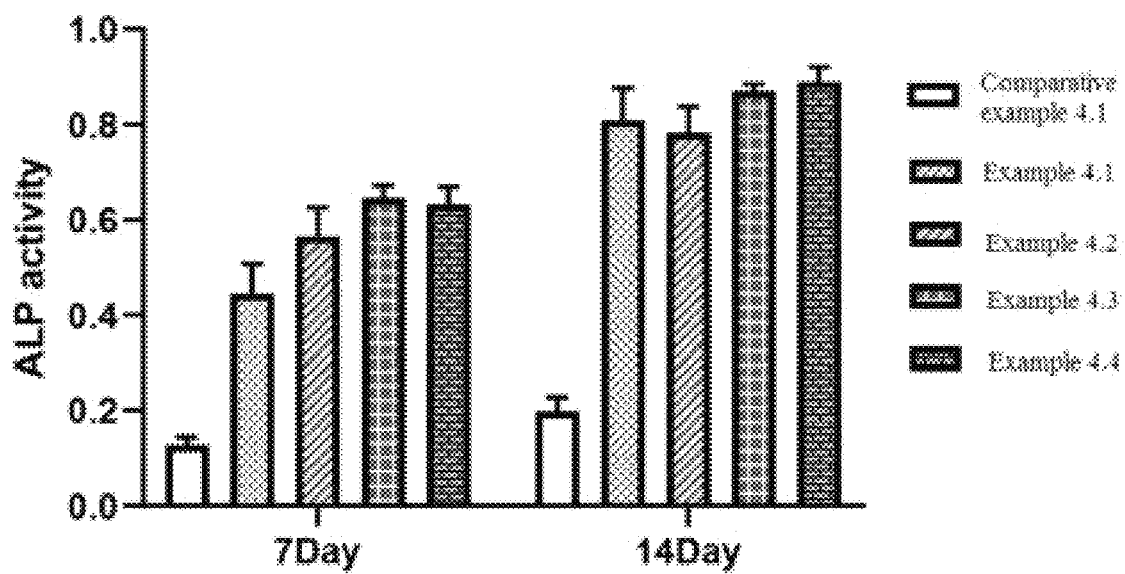
FIG. 12 is the ALP activity test in Comparative example 4.1 and Examples 4.1 to 4.4 of the present disclosure.

The ALP activity detection of the materials in Comparative example 4.1 and Examples 4.1 to 4.4 is shown in FIG. 12.

As shown in FIG. 12: the cellular ALP activity in the test of the materials in Examples 4.1 to 4.4 was significantly higher than that in Comparative example 4.1, which was due to the addition of inorganic nanomaterials with osteogenic activity to the absorbable bioactive bone cement of the present disclosure. Bioactive inorganic nanomaterials could be gradually exposed or released as the bone cement degraded in vivo, thereby contacting with the surrounding tissue environment to show osteogenic activity.

As can be seen from the above examples, the present disclosure provides an absorbable bioactive bone cement, comprising a component A and a component B; the component A comprises a cycloketene acetal compound and an oxidizing agent; the component B comprises a hydrophobic vinyl monomer, a hydrophilic cross-linking agent, and an inorganic nanomaterial-supported reducing agent. The bone cement provided by the present disclosure is formed by in-situ curing of free radical ring-opening polymerization reaction in the human body environment, the reaction process is rapid, the reaction is slightly exothermic and will not burn the human body, and the subsequent use thereof will not cause loosening. The added inorganic nanomaterial has osteogenic activity and can be absorbed by the human body, which can be degraded and absorbed with free radical ring-opening polymer of cycloketene acetal compound in a physiological environment. However, the absorption time of the inorganic nanomaterial is longer, avoiding the deficiency of too short degradation time of the calcium phosphate bone cement and calcium sulfate bone cement, which is suitable for total joint replacement, vertebroplasty, bone defect reconstruction, treatment of infectious diseases, etc.

The above are only the preferred embodiments of the present disclosure. It should be noted that for those of ordinary skill in the art, several improvements and modifications can be further made without departing from the principle of the present disclosure, which should also be regarded as the protection scope of the present disclosure.

The invention claimed is:

1. A medical adhesive comprising a component A and a component B:
   The component A comprises a cycloketene acetal compound and an oxidizing agent; and the component B comprises a vinyl monomer, a cross-linking agent and a reducing agent;
   wherein the cycloketene acetal compound is selected from one or more of 2-methylene-1,3-dioxepane, 2-methylene-4-phenyl-1,3-dioxolane, 5,6-benzo-2-methylene-1,3-dioxepane and 4,7-dimethyl-2-methylene-1,3-dioxepane;
   the oxidizing agent is selected from one or more of benzoyl peroxide, tert-butyl hydroperoxide, ammonium persulfate and hydrogen peroxide;
   the vinyl monomer is selected from one or more of (meth)acrylic acid, (meth)acrylate, vinyl acetate, maleimide polyethylene glycol carboxylic acid, biotin-PEG-6-maleimide, m-maleimidobenzoyl-N-hydroxysulfosuccinimide ester, 6-maleimidohexanoic acid, ethylene glycol vinyl ether, tetramethylene glycol monovinyl ether, vinyl (2-chloroethyl) ether, meth)acryloyloxy-phosphorylcholine, 10-(phosphonooxy) decyl methacrylate, sulfobetaine methacrylate, 4-methacryloyloxyethyl trimellitic anhydride, dopamine methacrylamide, N-acryloyl(trimethylol)aminomethane, poly(ethylene glycol) methacrylate, 2-(N,N-dimethylamino)ethyl methacrylate, (meth)allylamine and O-allylhydroxylamine;
   the cross-linking agent is a monomer containing two or more vinyl units, for example, selected from one or more of ethylene glycol dimethacrylate, methacrylic anhydride, diallyl maleate, bis (2-methacryloxyethyl) phosphate, tri (ethylene glycol)divinyl ether, diallylamine, triallylamine, N-methyldiallylamine, 1,5-hexadiene, diallyl disulfide and diallyldimethylsilane; and/or
   the reducing agent is selected from one or more of N,N-dimethyl-p-toluidine, N,N-dimethylaniline, sodium metabisulfite, sodium bisulfite and ferrous sulfate.

2. The medical adhesive according to claim 1, wherein the molar ratio of the cycloketene acetal compound to the vinyl monomer is 100:1 to 1:100;
   the mass of the cross-linking agent accounts for 0.2 wt % to 60 wt % of the total mass of the cycloketene acetal compound and the vinyl monomer;
   the mole number of the oxidizing agent accounts for 0.01 wt % to 10% of the total mole number of the cycloketene acetal compound and vinyl monomer; and/or
   the mole number of the reducing agent accounts for 0.01% to 10% of the total mole number of the cycloketene acetal compound and the vinyl monomer.

3. The medical adhesive according to claim 1, wherein the molar ratio of the vinyl monomer to the cycloketene acetal compound is 0.01 to 100:1;
   the molar ratio of the cross-linking agent to the cycloketene acetal compound is 0.001 to 0.2:1;
   the molar ratio of the oxidizing agent to the cycloketene acetal compound is 0.001 to 0.2:1; and/or
   the molar ratio of the oxidizing agent to the reducing agent is 0.01 to 10:1.

4. The medical adhesive according to claim 1, wherein the component B further comprises an antibacterial agent;
   the antibacterial agent is selected from penicillins, cephalosporins, aminoglycosides, macrolides, lincomycins, quinolones, tetracyclines, sulfonamides, silver ions, zinc ions, antibacterial peptide, coumarin compound, polyguanidine polymers and benzalkonium chloride; and/or
   the molar ratio of the antibacterial agent to the cycloketene acetal compound is $1 \times 10^{-8}$ to $1 \times 10^{-4}$:1 or $1 \times 10^{-5}$ to $1 \times 10^{-4}$:1.

5. The medical adhesive according to claim 1, which is a fast-curing and degradable strong bone adhesive.

6. The medical adhesive according to claim 5, wherein the component B further comprises an osteogenic active ingredient; wherein
   the osteogenic active ingredient is selected from one or more of hydroxyapatite, calcium triphosphate, bioactive glass, mesoporous silica, BMP-2, BMP-7, strontium ion, zinc ion, magnesium ion, bisphosphonate, dexamethasone, tacrolimus, and simvastatin; and/or
   the osteogenic active ingredient accounts for 0.01 wt % to 100 wt % of the cycloketene acetal compound.

7. The medical adhesive according to claim 1, which is an absorbable rapid hemostatic adhesive, further comprising a hemostatic agent;
   wherein the hemostatic agent is selected from one or more of vitamin k1, vitamin k4, haemocoagulase, sodium carboxysulfonate, aminocaproic acid, carbazochrome and halloysite, and/or
   the molar ratio of the hemostatic agent to the cycloketene acetal compound is $1 \times 10^{-7}$ to $1 \times 10^{-4}$:1.

8. The medical adhesive according to claim 1, which is an absorbable medical soft tissue adhesive, further comprising a substance for promoting tissue and organ healing.

9. The medical adhesive according to claim 8, wherein
   the substance for promoting the tissue and organ healing is selected from one or more of β-1,3-glucan and derivatives thereof, hyaluronic acid and asiaticoside; and/or
   the molar ratio of the substance for promoting the tissue and organ healing to the cycloketene acetal compound is $1 \times 10^{-8}$ to $1 \times 10^{-4}$:1.

10. The medical adhesive according to claim 1, which is an absorbable bioactive bone cement, wherein the reducing agent is an inorganic nanomaterial-supported reducing agent.

11. The medical adhesive according to claim 10, wherein the vinyl monomer is selected from one or more of acrylate, methacrylate, N-tert-butylacrylamide, N-dodecylacrylamide, 3-(methacryloyloxy) propyltrimethoxysilane and vinyl acetate;
   the cross-linking agent is selected from one or more of poly(ethylene glycol) dimethacrylate, polyethylene glycol diacrylate, diacrylamide polyethylene glycol, dimethacrylamide polyethylene glycol, phosphate dimethacrylate and phosphate diacrylate;
   and/or the inorganic nanomaterial in the inorganic nanomaterial-supported reducing agent is selected from one or more of nano-hydroxyapatite, nano-calcium triphosphate and nano-bioactive glass.

12. A method of hemostasis comprising applying the medical adhesive according to claim 7 to a site in need of hemostasis.

13. The method according to claim 12, wherein the site in need of hemostasis is selected from the group consisting of skin, organs and blood vessels.

14. A method of adhesion of a wound site comprising applying the medical adhesive according to claim 8 to the wound site.

15. The method according to claim 14, wherein the wound site is a wound of tissue, organ, or skin.

16. A method of treating a bone injury site comprising applying the medical adhesive according to claim 11 to the bone injury site.

17. The method according to claim 16, wherein applying the medical adhesive to the bone injury site comprises applying the adhesive when the adhesive is in a dough phase.

* * * * *